(12) United States Patent
Limaye et al.

(10) Patent No.: US 12,370,324 B2
(45) Date of Patent: Jul. 29, 2025

(54) PEN NEEDLE

(71) Applicant: Embecta Corp., Andover, MA (US)

(72) Inventors: Amit Uday Limaye, Wayne, NJ (US);
David Poganski, Aimont, NY (US);
David Huang, Hayward, CA (US);
Brishell Aquise, Oakland, CA (US)

(73) Assignee: Embecta Corp., Parsippany, NJ (US)

( * ) Notice: Subject to any disclaimer, the term of this patent is extended or adjusted under 35 U.S.C. 154(b) by 554 days.

(21) Appl. No.: 17/618,686

(22) PCT Filed: Jun. 18, 2020

(86) PCT No.: PCT/US2020/038350
§ 371 (c)(1),
(2) Date: Dec. 13, 2021

(87) PCT Pub. No.: WO2020/257398
PCT Pub. Date: Dec. 24, 2020

(65) Prior Publication Data
US 2022/0241516 A1 Aug. 4, 2022

Related U.S. Application Data

(60) Provisional application No. 62/868,350, filed on Jun. 28, 2019, provisional application No. 62/864,116, filed on Jun. 20, 2019.

(51) Int. Cl.
*A61M 5/32* (2006.01)
*A61M 5/34* (2006.01)
*A61M 5/50* (2006.01)

(52) U.S. Cl.
CPC ........ *A61M 5/3202* (2013.01); *A61M 5/3213* (2013.01); *A61M 5/3221* (2013.01);
(Continued)

(58) Field of Classification Search
CPC .... A61M 2005/3254; A61M 2205/581; A61M 2205/582; A61M 5/3202; A61M 5/321; A61M 5/3213
See application file for complete search history.

(56) References Cited

U.S. PATENT DOCUMENTS 3,907,155 A 9/1975 Smith et al.
5,360,404 A * 11/1994 Novacek ............. A61M 5/3202
604/110

(Continued)

FOREIGN PATENT DOCUMENTS

EP 0903157 A2 3/1999
EP 2039384 B1 3/2009
(Continued)

OTHER PUBLICATIONS

Extended European Search Report in EP Application No. 2082783.9 dated Jun. 1, 2023.
(Continued)

*Primary Examiner* — William R Carpenter
(74) *Attorney, Agent, or Firm* — Greenberg Traurig, LLP; David J. Dykeman; Roman Fayerberg

(57) ABSTRACT

A pen needle (10) includes a hub (12) supporting a needle (30), an inner shield (14) enclosing the distal end of the needle, and an outer cover (16). The outer surface of the hub can include ribs (66) that cooperate with ribs (72) on the inner surface of the outer cover to assist in attaching the pen needle to a delivery device while preventing over torqueing or over tightening. In one embodiment, the inner shield (14) has a dimension to attach to the distal end of the hub (12) after use to enclose the proximal, non-patent end of the needle. In another embodiment, the outer cover (16)
(Continued)

includes a closure member that can be removed during use and re-attached after use to cover the proximal end of the needle.

15 Claims, 21 Drawing Sheets

(52) U.S. Cl.
CPC .......... *A61M 5/3245* (2013.01); *A61M 5/343* (2013.01); *A61M 5/347* (2013.01); *A61M 5/5086* (2013.01); *A61M 2005/3254* (2013.01)

(56) References Cited

U.S. PATENT DOCUMENTS

| | | | |
|---|---|---|---|
| 5,391,150 A * | 2/1995 | Richmond | A61J 1/10 604/91 |
| 5,941,857 A | 8/1999 | Nguyen et al. | |
| 5,968,021 A * | 10/1999 | Ejlersen | A61M 5/3213 604/199 |
| 7,645,264 B2 | 1/2010 | Marsh et al. | |
| 8,057,444 B2 * | 11/2011 | Hartmann | A61M 5/3213 604/110 |
| 9,775,944 B2 | 10/2017 | DiBiasi | |
| 11,207,472 B2 * | 12/2021 | Rini | A61M 5/3293 |
| 2004/0153038 A1 * | 8/2004 | Guala | A61M 39/14 604/263 |
| 2005/0033230 A1 | 2/2005 | Alchas et al. | |
| 2007/0149924 A1 * | 6/2007 | Marsh | A61M 5/002 604/117 |
| 2009/0069753 A1 * | 3/2009 | Ruan | A61M 5/3213 604/192 |
| 2009/0069755 A1 * | 3/2009 | Horvath | A61M 5/46 604/240 |
| 2012/0022460 A1 | 1/2012 | Horvath et al. | |
| 2012/0071835 A1 * | 3/2012 | Marshall | A61M 5/3202 604/192 |
| 2015/0297837 A1 * | 10/2015 | Schraga | A61M 5/34 604/239 |
| 2015/0321326 A1 * | 11/2015 | Nino | B25B 23/1427 81/475 |
| 2016/0101241 A1 | 4/2016 | Ruan et al. | |
| 2017/0021110 A1 * | 1/2017 | Srinivasan | A61M 5/002 |
| 2017/0106136 A1 * | 4/2017 | DiBiasi | A61M 5/002 |
| 2019/0003716 A1 | 1/2019 | Je et al. | |
| 2019/0083716 A1 | 3/2019 | Saxe | |

FOREIGN PATENT DOCUMENTS

| | | |
|---|---|---|
| EP | 2420271 B1 | 2/2012 |
| WO | 2019033092 A1 | 2/2019 |
| WO | 2020038350 A1 | 12/2020 |

OTHER PUBLICATIONS

International Search Report dated Sep. 9, 2020, which issued in the corresponding PCT Patent Application No. PCT/US2020/038350.

* cited by examiner

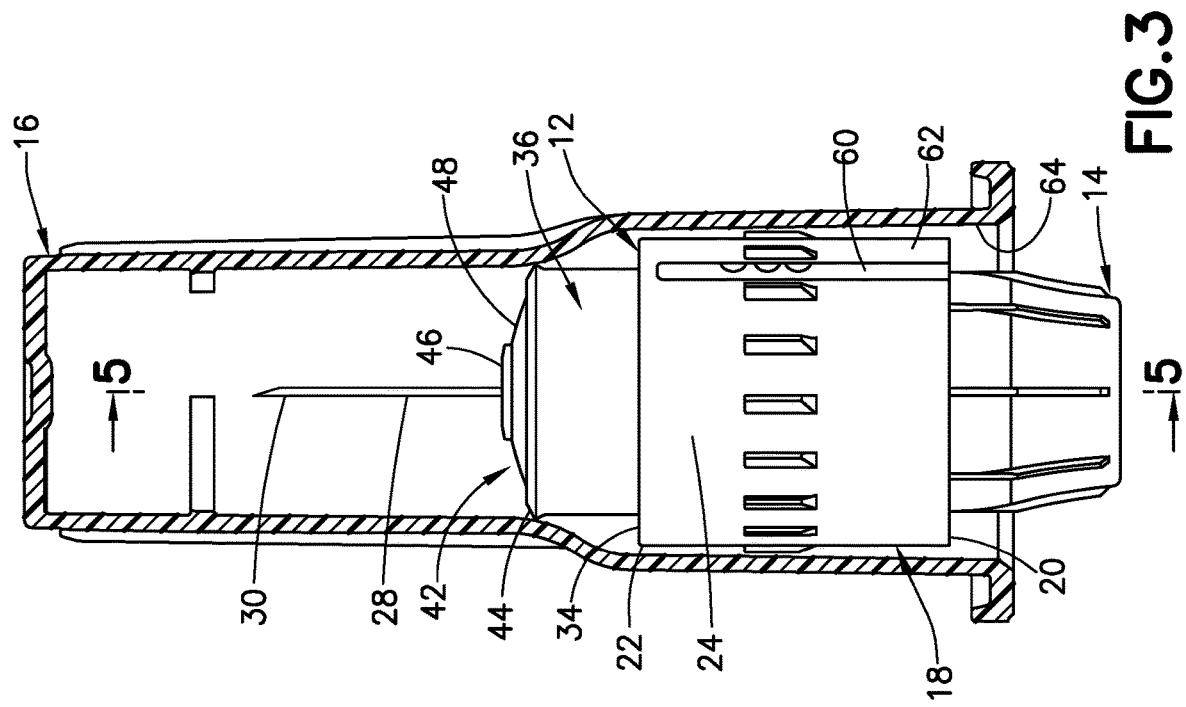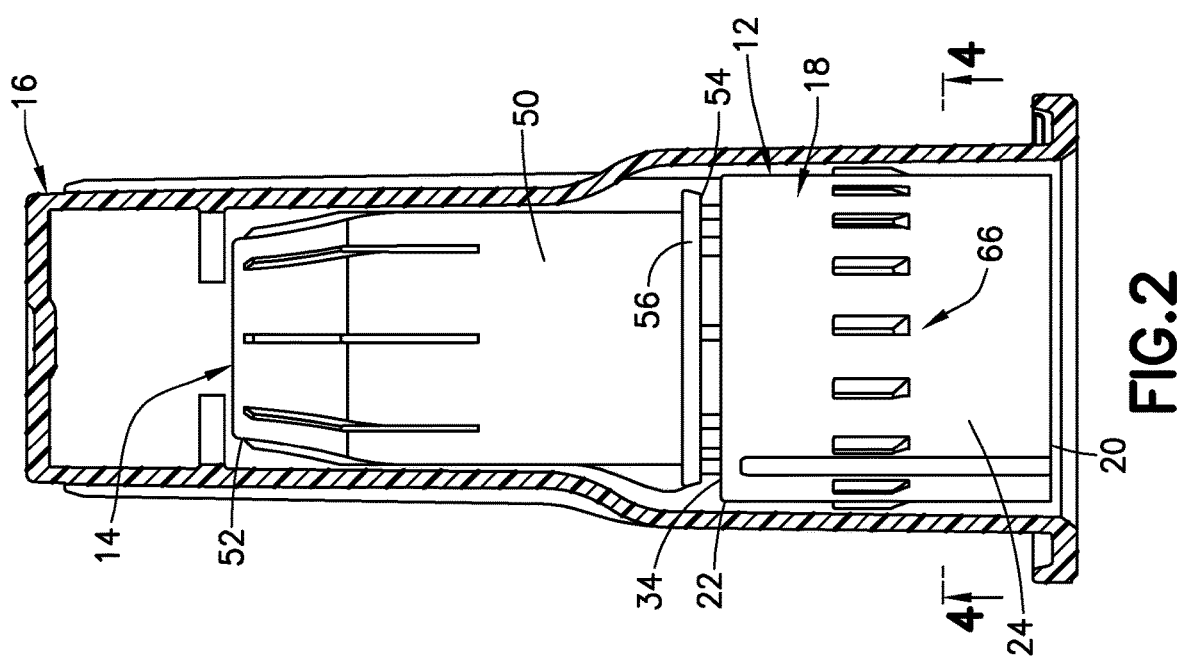

PEN NEEDLE

This application claims priority to U.S. Provisional Application No. 62/868,350, filed on Jun. 28, 2019, and U.S. Provisional Application No. 62/864,116, filed on Jun. 20, 2019, which are hereby incorporated by reference in their entireties.

BACKGROUND

Field of the Invention

The disclosure is directed to a pen needle for attachment to a medication delivery device, such as a medication delivery pen. The pen needle can have a needle hub and an outer cover that includes a haptic feature, such as a tactile and/or audible indicator to avoid over tightening of the needle hub on the delivery pen. The pen needle can also have removable closure or end cap to close the open end of the needle hub.

Description of the Related Art

Pen needles are used to attach to a medication pen and are especially useful for delivering self-administered injectable medications such as insulin. In one known commercial device, a needle-bearing hub is provided inside a funnel-shaped outer cover, sometimes referred to as the outer shield, outer cover, or simply as the cover. The cannula or needle is affixed in an axial bore of the hub with one end protruding from the distal or "patient side" of the hub for injecting the patient and the other end of the needle is recessed in a cavity on the proximal or "non-patient" side of the hub, and is adapted for attachment to the medication pen. A paper and foil "eardrop" label is sealed on the edge of the open end of the funnel shaped outer cover. In addition, the medication pen may have a cap received over the distal end of the medication pen, over the opening where the pen needle is installed. To install the pen needle on a medication pen, the user removes the medication pen cap. The user then removes the label on the pen needle outer cover and holds the outer cover to install the hub, typically threading the hub onto the pen. Once the hub is installed on the medication pen, the outer cover can be removed by pulling the outer cover distally off the hub. A separate inner needle shield sits over the needle, which the user must remove to administer an injection. The inner shield generally sits on the hub and simply helps the user locate the needle without forming a sterility barrier. After use, the user may use the outer cover to unthread the hub from the pen and dispose of the pen needle.

Medication pens and associated pen needles are disclosed in U.S. Pat. No. 7,645,264, and U.S. Patent Application Publication Nos. 2009/0069755 and 2012/0022460, all of which are incorporated by reference in their entirety for their teaching of pen needle design and construction. A device for arranging a releasable pen needle on an injection pen and releasing the pen needle into a mating storage or disposal container is disclosed in U.S. Pat. No. 8,057,444, also incorporated by reference.

Pen needles can include a cover or shield to cover the end of the needle to prevent re-use and accidental needle stick. Pen needles are also known that have a shield to cover the proximal end of the needle when the pen needle is separated from the delivery device.

While the prior devices are generally suitable for the intended use, there is a need in the industry for improvements to the pen needles.

SUMMARY

The present disclosure is directed to a pen needle assembly for use with a medication delivery device for injecting a medication into a patient. The pen needle in one embodiment has a hub with a needle, an inner needle shield, and an outer cover.

One feature of the pen needle is a needle hub and outer cover that includes a mechanism providing haptic feedback to the user when the hub is threaded onto the delivery pen. The mechanism providing the haptic feedback can be a protrusion formed on the outer surface of the needle hub and a protrusion on the inner surface of the outer cover where the protrusions engage to slide over one another to limit over tightening when attaching the pen needle to the delivery pen. The protrusions slide over one another when tightening the hub on the delivery pen to provide a tactile and/or audible sensation to the user. The protrusions engage sufficiently to assist in removing the hub from the delivery pen without slipping. The protrusions have a suitable configuration for sliding over another to resist over tightening while enabling separation of the hub from the pen needle. The protrusions can be in the form of tabs, detents, ribs or other suitable configuration.

The haptic feedback mechanism can be longitudinally extending ribs on the outer surface of the needle hub where the ribs have surfaces that allow a complementing rib or detent on the outer cover to slide over the ribs in one rotational direction when attaching the pen needle to the delivery pen and resist sliding in an opposite rotational direction when separating the pen needle from the delivery pen. The protrusions on the needle hub can have one face that is inclined relative to the longitudinal axis of the needle hub. The protrusions can also have a leading face that is inclined or sloping relative to the outer wall of the hub and a trailing face that is substantially perpendicular to outer wall of the hub. The radial outer face of the protrusions can be inclined where the trailing face is spaced radially outward relative to the leading face of the protrusion.

The protrusions can be longitudinally extending ribs formed on the outer surface of the side wall of the hub and on an inner surface of the outer cover. The ribs can extend substantially parallel to the longitudinal axis of the hub and outer cover and have a longitudinal length greater than a width. The ribs can be spaced from the distal end and spaced from the proximal end of the outer cover and hub.

The inner shield can be removed to expose the patient end of the needle during use. After removing the used pen needle from the delivery pen, the inner shield can then be attached to the non-patient end of the needle hub to enclose the non-patient end of the needle. The inner shield can be inserted into the open end of the needle hub and coupled to the needle hub by a friction fit or interference fit.

The needle hub can have aside wall in internal threads for coupling with the delivery pen. The side wall can have one or more open slots extending in the longitudinal direction to form wall sections that are able to flex outwardly in a radial direction with respect to the delivery pen for removal from the delivery pen. The outer cover has an open end that can be positioned on the needle hub after use to cover the patient end of the needle to reduce the occurrence of inadvertent needle stick. The inner surface of the outer cover includes an inwardly extending lip or detent that mates with the bottom edge of the needle hub when the outer cover is placed over the used pen needle. Pulling on the outer cover in a direction away from the delivery pen pulls the flexible wall section outwardly from the delivery pen allowing the threads to separate from the delivery pen where the used pen needle can be removed and discarded.

A removable closure or end cap can be coupled to the open end of the outer cover to enclose the pen needle. After use, the pen needle hub is returned to the outer cover and the end cap is attached to the open end of the outer cover to enclose the used pen needle for disposal. The end cap can have a tamper evident feature to indicate that the pen needle has been used. The end cap can include one or more tabs or flanges to assist in removing the end cap from the outer cover and replacing the end cap onto the outer cover. The end cap has an open end complementing the open end of the outer cover coupling the end cap to the outer cover.

The outer cover can have an axial length at least equal to the axial length of the needle hub and has a cavity sufficient to enclose the needle hub and needle before use and after use. The outer cover can have an axial length less than the axial length of the needle hub where the outer cover couples to a distal end of the needle hub to cover the needle without enclosing the open end of the needle hub.

A pen needle can comprises a hub having a distal end, and an open proximal end for attachment to a delivery device, a needle coupled to the hub and having a distal end extending from the distal end of the hub. A removable inner shield is coupled to the hub, where the inner shield has a side wall with an inner surface complementing an outer surface of the hub and where the inner shield is configured to be coupled to the outer surface at a distal end of the hub for covering the distal end of the needle. The inner shield has an outer surface with a dimension for coupling with an inner surface of the open proximal end of the hub.

The pen needle can comprise a hub having aside wall, a proximal end for attachment to a delivery device, and a distal end. The side wall includes a plurality of longitudinally extending ribs projecting radially outward and have an inclined leading face oriented in a plane parallel to a longitudinal axis of the hub, and a trailing face oriented in the plane parallel to the longitudinal axis of the hub. A needle is coupled to the hub and has a distal end extending from the distal end of the hub and a proximal end at a proximal end of the hub. An outer cover has a side wall with an inner surface having longitudinally extending ribs. The ribs project radially inward and have a longitudinally extending leading face oriented at an incline with respect to a radius of the outer cover, and a trailing face extending parallel to the longitudinal axis of the outer cover.

These and other aspects and features of the pen needle will be apparent from the following detailed description of the invention and the drawings.

BRIEF DESCRIPTION OF THE DRAWINGS

The following is a brief description of the drawings, in which:

FIG. 2 is a partial cross sectional view showing the pen needle of FIG. 1;

FIG. 3 is a cross sectional view of the pen needle of FIG. 2 showing the inner shield on the proximal end of the hub after use;

Figure 1:
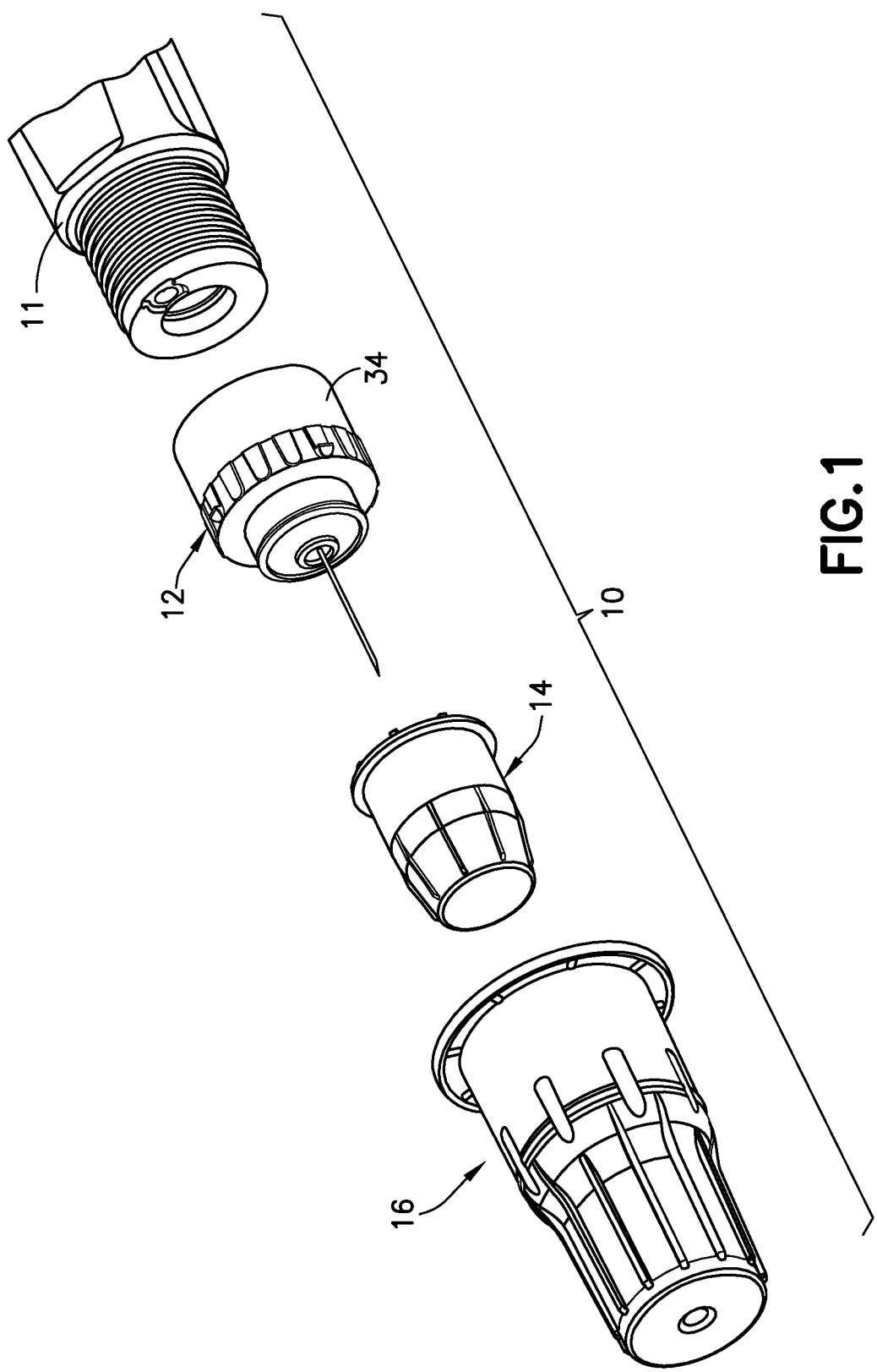
FIG. 1 is an exploded view of the pen needle.

The figures are not to scale, and some features are omitted in certain views to better illustrate other features.

DETAILED DESCRIPTION

As used herein, the "distal" direction is in the direction of the injection site, and the "proximal direction" is the opposite direction. The "axial" direction is along the longitudinal axis of the device. The needle cannula is generally arranged axially in the device. "Radially" is a direction perpendicular to the axial direction and in a plane extending from the center axis of the device. Thus, "radially inward" generally means closer to the needle. "Circumferentially" refers to arranging around the circumference, so that threads are arranged circumferentially on the end of a threaded fitting. The "top" view of a pen needle is looking at the pointed end of the needle. The different features of the embodiments can be used in combination with and used with other embodiments as long as the combined parts are not inconsistent with or interfere with the operation of the device and assembly.

A medication pen or delivery pen is used herein to refer to a device having a medication compartment, typically containing multiple doses of medication, and a separate pen needle. The phrase "pen needle" refers to a needle-bearing assembly, which can be attached to the medication pen body so that a proximal end of the pen needle assembly accesses a medication compartment and a distal end is adapted for insertion into an injection site to perform one or more injections. The terms "needle" and "cannula" are used herein interchangeably to refer to a thin tubular member having a sharpened end for insertion into an injection site on a subject. As used herein, the "distal" direction is in the direction toward the injection site, and the "proximal" direction is the opposite direction. "Axial" means along or parallel to the longitudinal axis of the pen needle and the "radial" direction is a direction perpendicular to the axial direction.

This disclosure is not limited in its application to the details of construction and the arrangement of components set forth in the following description or illustrated in the drawings. The embodiments herein are capable of being modified, practiced or carried out in various ways. It will be understood that the phraseology and terminology used herein is for the purpose of description and should not be regarded as limiting. The use of "including," "comprising." or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not limited to physical or mechanical connections or couplings. Further, terms such as up, down, bottom, and top are relative, and are to aid illustration, but are not limiting. The embodiments are not intended to be mutually exclusive so that the features of one embodiment can be combined with other embodiments as long as they do not contradict each other. Terms of degree, such as "substantially", "about" and "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely present in the structure.

Referring to the drawings, a pen needle 10 includes a needle hub 12. An outer cover 16 can be included that fits over the pen needle 10 during storage and assists in attaching the pen needle 10 to a delivery device, such as a delivery pen 11 shown in FIG. 1. A closure is generally provided over the open end of the cover to maintain the needle hub 12 in a sterile condition until ready for use. The closure can be the closure as shown in FIG. 2 that can be peeled from the needle hub 12 or a closure as shown in FIGS. 18-26 as described herein. The delivery pen can be a standard delivery pen or other medication delivery device as known in the art for dispensing and delivering a medication, such as insulin. An example of a suitable delivery pen is disclosed in U.S. Pat. No. 9,774,844, which is hereby incorporated by reference for this purpose.

As shown in FIGS. 1-18, the pen needle 10 includes the hub 12. The hub 12 is configured for supporting the inner needle shield 14. The hub can be a one-piece unit or made from separate components that are coupled together. In the pen needle shown, the hub 12 includes a hub body 18 with an open bottom end 18 defining the proximal non-patient end 20 for coupling with the delivery pen 11, and a distal end 22 forming the patient end of the pen needle. The open bottom end formed by the hub body 18 has a side wall 24 with internal threads 26, such an the threads shown in FIG. 10, for coupling to the delivery pen 11 in a known manner. The distal end 22 has an opening for a needle 28 or cannula and defines the skin contact surface during use.

Needle 28 can be a hollow steel needle with a sharpened tip at a distal end at a proximal end and has a gauge and length for penetrating the skin to a desired depth and delivery of a medication to a patient. The needle 28 has a patient end forming a distal end 30 with a sharpened tip extending from the distal end of the hub 12 for penetrating the skin of the patient. A proximal end of the needle 28 is positioned at the proximal end of the hub 12 for piercing a septum in the delivery device for receiving the drug or medication from the delivery device in a usual manner. The distal end 30 has an exposed length extending from the distal end of the hub during the injection of about 3-10 mm and typically about 4-6 mm.

Figure 5:
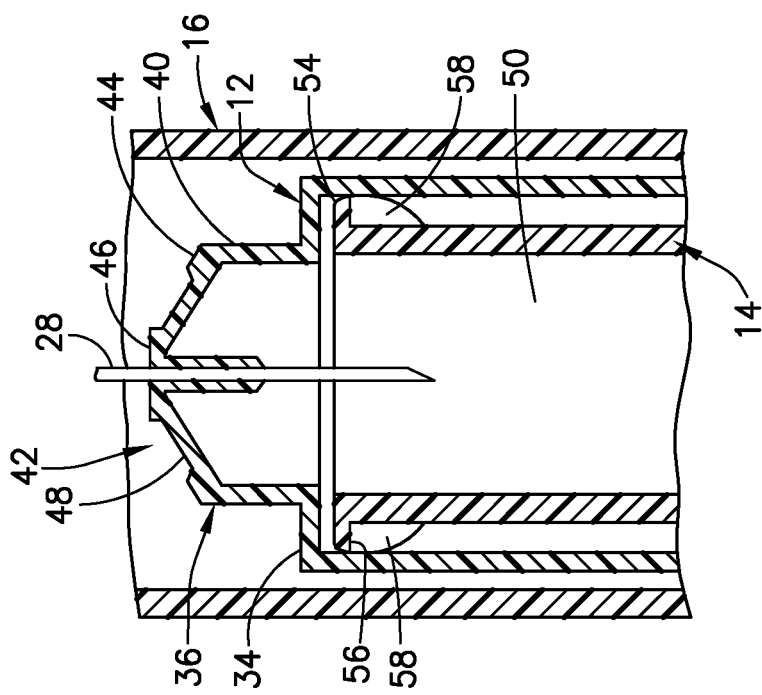
FIG. 5 is a partial cross sectional side view taken along line 5-5 of FIG. 3 of the needle hub with the inner shield inserted into the open end of the needle hub.
Figure 6:
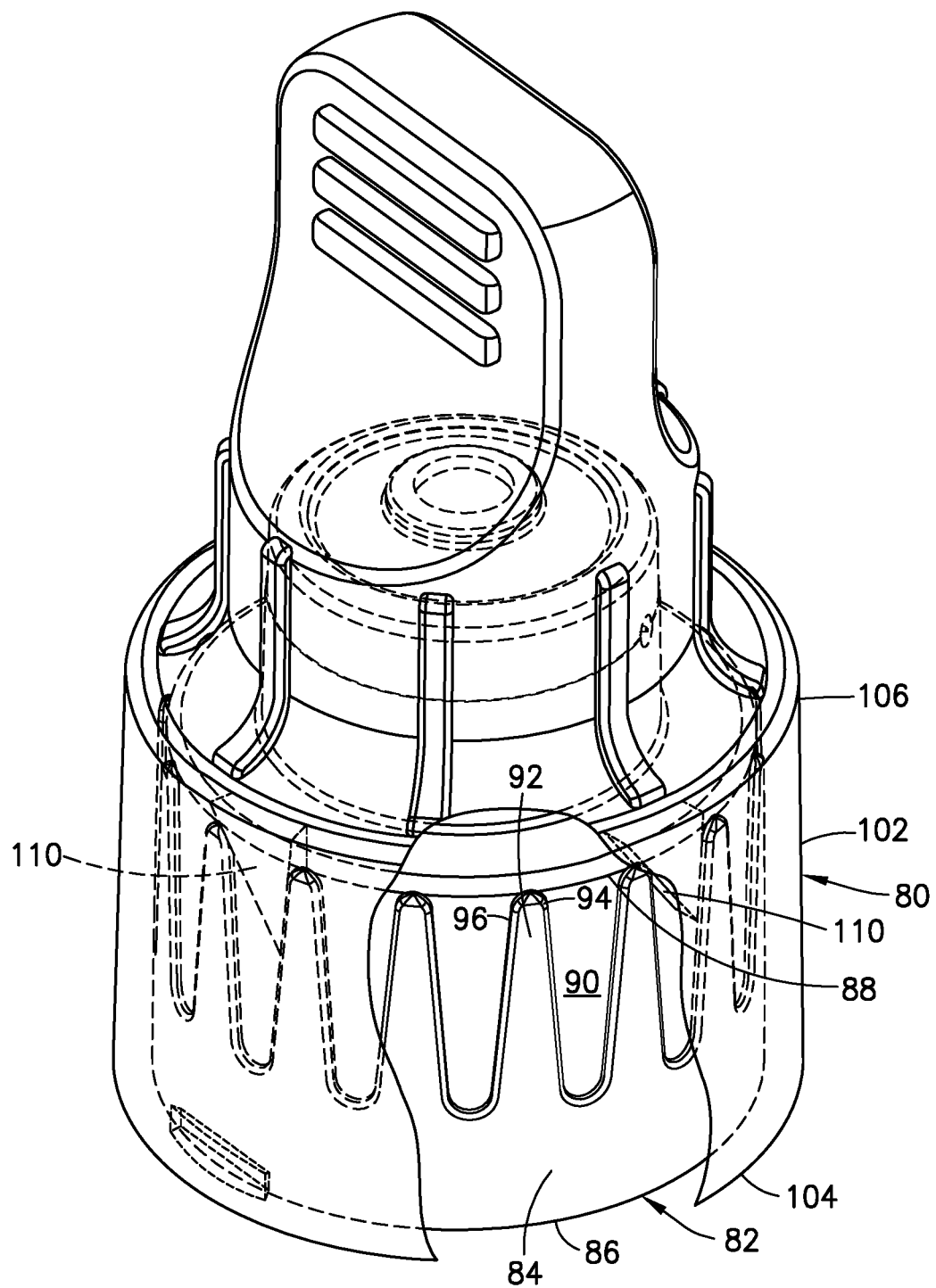
FIG. 6 is a perspective view of the pen needle in another embodiment.

Referring to FIGS. 3, 5, and 6, the hub body 18 has an end wall 34 at the top distal end of the side wall 24. The end wall has a distal face with a post 36 extending in the distal direction. The post 36 has an axial passage receiving and supporting the needle 28. The needle 28 is fixed to the post 36 by an adhesive in a usual manner. As shown, the post 36 has a substantially cylindrical configuration with a substantially cylindrical outer surface 40. The distal end of the needle 28 projects from the post 36 to extend distally from the pen needle a distance for penetrating the skin of the patient during an injection to a selected depth in the skin. The proximal end of the needle 28 extends within the hub body 18 a distance for connecting to a reservoir of the delivery device when the pen needle is attached to the delivery device.

The distal face 42 of the post 36 can form a skin contact surface to deform the surface of the skin during an injection. The distal face 42 can have various shapes and dimensions. The pen needle as shown has a convex configuration to control the shape of the indentation formed in the skin to control the depth of penetration of the needle. The distal face 42 has a raised outer peripheral ring 44 and a raised inner ring 46 forming an annular recess 48 between the outer ring 44 and the inner ring 46. The outer ring and the inner ring have a curved convex surface forming a continuous radius of curvature. The surface of the annular recess has a bottom surface with a radius of curvature that is concentric with the radius of curvature of the inner and outer rings.

As shown in FIG. 2, the inner shield 14 fits on the hub 12 to enclose the distal end of the needle 28. The inner shield 14 and hub 12 fit within the outer cover 16. A closure, such a tab that can be peeled from the hub, is provided at the open end of the outer cover to enclose the hub until ready for use. During use, the closure is removed to expose the open end of the hub 12. The hub 12 is threaded onto the threaded end of the delivery pen 11 using the outer cover 16 to assist in screwing the hub onto the delivery pen. When secured to the delivery pen and the fluid communication is obtained between the pen needle and the medication compartment of the delivery pen, the outer cover 16 is pulled free from the hub 12. The inner shield 14 is removed to expose the needle for injecting the medication to the patient. After use, the outer cover 16 is placed onto the hub where the outer cover grips the hub sufficiently so that the hub can be separated from the delivery pen where the used pen needle can be discarded.

As shown in FIGS. 1-3, the inner shield 14 has a substantially cylindrical side wall 50 with a closed distal end 52 and an open proximal end 54. External ribs can be included to assist the user in manipulating the inner shield during use. The side wall 50 has an inner surface with a dimension complementing the outer dimension and configuration of the post 36 so that the inner shield 14 fits onto the post 36 by a friction fit.

As shown in FIGS. 2 and 3, the proximal end of the side wall 24 of the inner shield 14 has a flange 56 projecting radially outward. At least one, and typically a plurality of radially extending detents shown as ribs 58 project from the side wall 24 of the inner shield 14 next to or adjacent the flange 56 as shown in FIG. 2. The ribs 58 can project radially outward a distance corresponding substantially to the radial dimension of the flange 56 or can extend a distance slightly greater than the radial dimension of the flange 56. The outer dimension of the flange 56 and the ribs 58 complement the inner dimension of the hub body 18. In one embodiment after use of the pen needle, the inner shield 14 can be inserted into the open end of the needle hub body 18 to cover the proximal end of the needle. The flange 56 and/or the ribs 56 have a dimension to engage the inner surface of the hub body 18 to retain the inner shield within the open end of the hub body by a friction or interference fit as shown in FIG. 3 and FIG. 5

The hub body 18 can have one or more longitudinal slots 60 forming a flexible wall portion 62 as shown in FIG. 3. The hub 12 is attached to the delivery pen by internal threads on the side wall of the hub 12. As shown in FIG. 3, the outer cover 16 has an inwardly extending projection 64 that can engage the proximal end of the side wall and the flexible portion 62. By pulling or twisting the outer cover 16 the projection 64 can deflect the flexible portion 62 radially outward to separate the internal threads from the threads on the delivery pen to assist in separating the hub from the delivery pen by a prying motion rather than solely by a rotational motion.

The needle hub 12 includes a ratcheting mechanism between the hub 12 and the outer cover 16 to assist in threading the needle hub onto the delivery pen and providing a limited slip between the outer cover and the hub to prevent over tightening or over torqueing of the hub onto the delivery pen. The ratcheting mechanism is able to grip the needle hub to unthread and separate the needle hub from the delivery pen.

Figure 4:
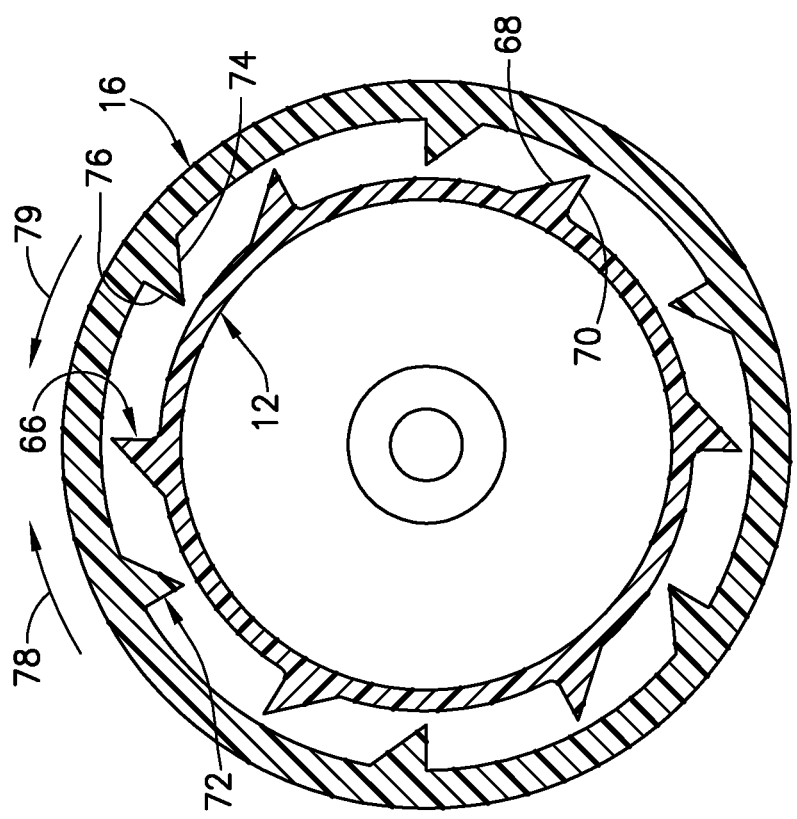
FIG. 4 is an end view in cross section of the pen needle taken along line 4-4 of FIG. 2.

As shown in the drawings, the ratcheting mechanism can be in various forms. As shown in FIG. 2-4 the outer surface of the hub body 18 has a plurality of projections that cooperate with corresponding projections on the inner surface of the outer cover 16. In the ratcheting mechanism shown, the projections on the side wall 24 of the hub body 18 extend in a longitudinal direction relative to the longitudinal axis of the hub body 18. The projections form ribs 66 that project radially outward and extend in the longitudinal direction of the hub. In the embodiment shown, the ribs 66 are positioned in a center portion of the side wall 24 although ribs can be located in other areas of the side wall.

The ribs 66 have a shape and dimension to allow the outer cover 16 to engage the hub 14 to rotate the hub 12 relative the delivery pen for attachment and separation of the needle hub. The ribs 66 have a leading face 68 and trailing face 70. As shown, the leading face 68 is a flat surface oriented in a plane at an inclined angle relative to a radius of the hub 12 as shown in FIG. 4. The leading face 68 extends outwardly at an incline from the outer surface of the side wall of the hub 12 to form a sloped surface relative to the outer surface of the hub. The trailing face 70 is oriented in a radial direction of the center axis of the hub 12. As shown, leading face 68 and the trailing face 70 form an acute angle relative to each other.

The outer cover 16 has inwardly extending ribs 72 that complement the ribs 66. The ribs 72 project inwardly from an inner surface of the outer cover as shown in FIG. 4. The ribs 72 have a leading face 74 and trailing face 76 that mate with the respective faces of the hub when the outer cover is rotated with respect to the hub in a first direction and in a second direction. The leading face 74 of the ribs 72 are oriented substantially parallel to the leading face 68 of the hub 12 and the trailing face 76 is oriented substantially parallel to the trailing face 70 of the hub. The leading face 74 is oriented at an inclined angle with respect to the radius of the outer cover 16 to project inwardly from the side wall. The trailing face 76 is oriented in a radial direction with respect to the longitudinal axis of the outer cover to project radially inward relative to the outer cover.

During use, the open proximal end of the hub 12 is threaded onto the threaded end of the delivery pen. The hub 12 is retained in the outer cover 16 and the outer cover is rotated relative to the delivery pen in the direction of arrow 78 to thread the hub 12 onto the delivery pen. The inclined leading faces 68 and 74 contact each other while threading the hub 12 onto the delivery pen. When the hub 12 is seated tightly on the delivery pen, the resistance relative to the outer cover 16 allowed the inclined leading faces 69 and 74 to slide over one another to prevent over tightening of the hub 12 on the delivery pen. The leading faces 69 and 74 slide over one another to produce a tactile and/or audible indication that the hub is threaded tightly on the delivery pen. The outer cover 16 is then removed to expose the needle for injecting the patient.

After the injection the outer cover 16 can placed on the hub 12 and the outer cover rotated in the direction of arrow 79. The trailing faces 70 and 76 engage one another without slipping to separate the hub from the delivery pen. The outer cover and hub then can be discarded. The hub and the outer cover are made of a suitable plastic material that is sufficient rigid for supporting the needle and attachment to the delivery pen. The plastic material allows sufficient flexing and deformation of the ribs to allow the ribs to slide over one another while maintain the integrity to enable removal form the delivery pen.

FIGS. 6-9 illustrate another embodiment of the ratcheting mechanism between an outer cover 80 and a hub 82. The ratcheting mechanism of FIGS. 6-9 can be used in the pen needle of FIGS. 1-5. The hub 82 includes a substantially cylindrical side wall 84 with an open bottom end 86 and a top end 88. The distal end and contact face of the hub 82 is similar to the hub of the previous embodiment so that similar elements are identified by the same reference numbers where needed. The side wall 84 includes a plurality of spaced apart recesses 90 forming raised ribs 92 for assisting the patient in gripping the outer surface of the hub 82. The ribs 92 have a substantially V-shape forming V-shaped recesses that are open to the distal end of the hub and converge toward the proximal end of the hub. The ribs 92 have a leading face 94, a trailing face 96, and a distal end 98.

Figure 7:
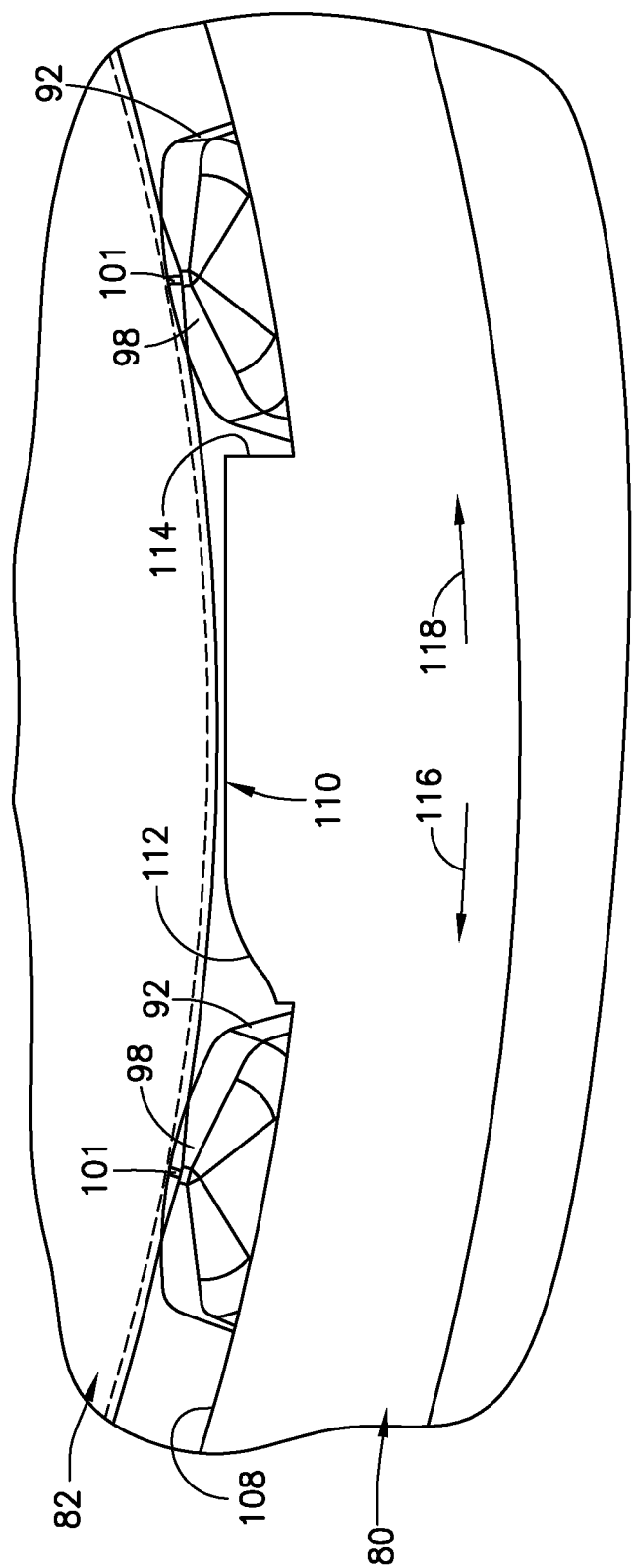
FIG. 7 is a partial end view of the pen needle ribs and inner surface of the cover of the embodiment of FIG. 6.
Figure 8:
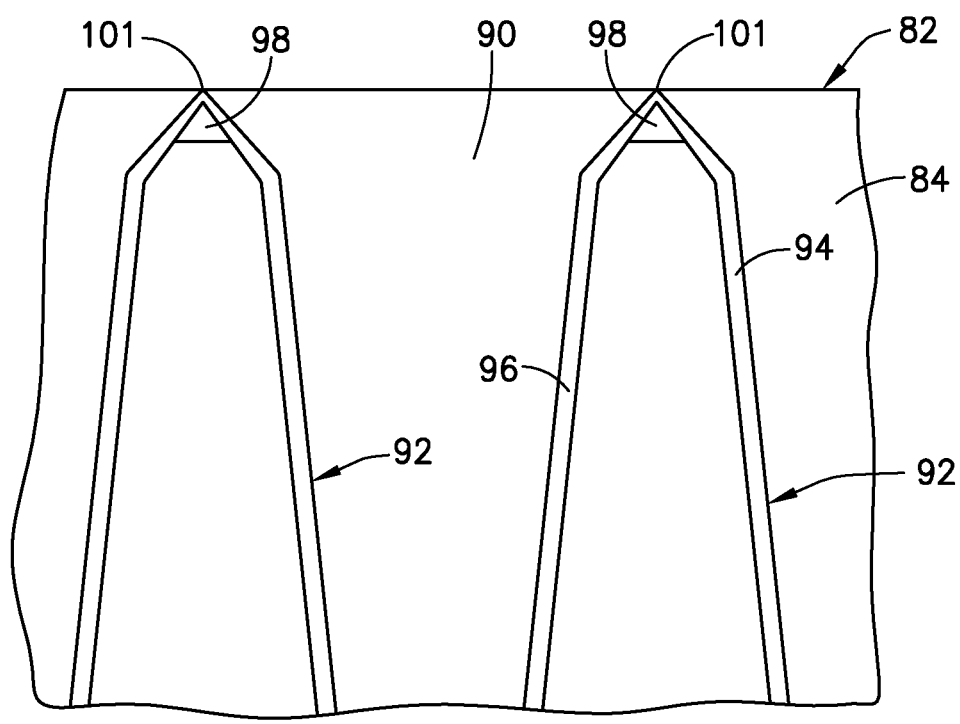
FIG. 8 is a partial elevational view of the outer surface of the hub of FIG. 6.
Figure 9:
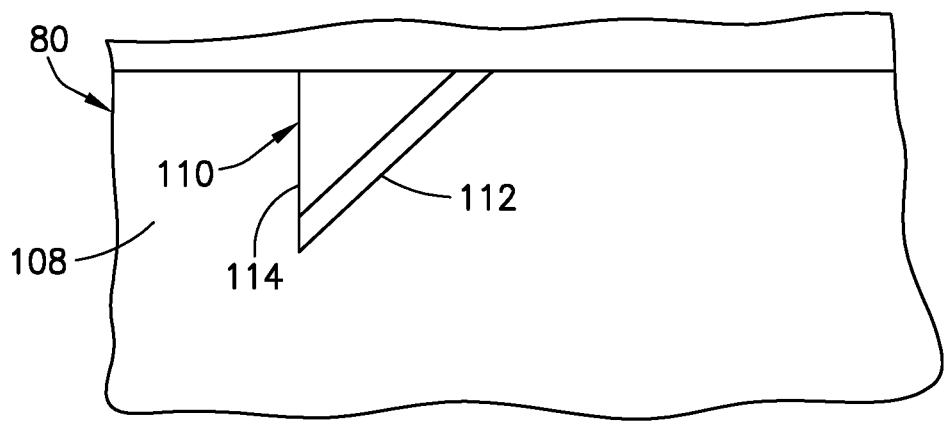
FIG. 9 is an enlarged elevational view of the rib on the cover of FIG. 6.

The leading face 94 is inclined relative to an outer radial surface 100 of the rib 92 to form a sloped surface extending between the face of the recess 90 and the outer surface 100. The trailing face 96 is also inclined relative to the radial outer surface 100 of the side wall 84 to form a sloped surface extending between the face of the recess 90 and the outer surface 100. As shown in FIG. 6, the leading faces 94 and the trailing faces 96 are further oriented at an incline relative to the longitudinal axis of the hub 82 and at an incline with respect to the radius of the hub. The leading faces and trailing faces are at an incline with respect to each other where the leading face of a first rib faces the trailing face of a second adjacent rib so that the ribs form a cam-like surface. The distal end of the leading and trailing faces have rounded surfaces as shown in FIG. 7 that converge at a distal tip 101.

The outer cover 80 has a cylindrical side wall 102 complementing the side wall 84 of the hub 82. The side wall 102 has an open proximal end 104 and a distal end 106. The inner surface 108 of the side wall 102 includes a plurality of spaced apart projections 110 for mating with the ribs 92 of the hub 82. The projections 110 form ribs that extend from the distal end 106 of the side wall 102 toward the proximal end 106. In the embodiment shown, the projections 110 have a substantially triangular shape with leading face 112 converging toward a trailing face 114 to an apex forming a tip 118. The leading face 112 forms an inclined surface extending between the inner surface 108 and the outer surface 116 of the projection 106. The leading face 112 is inclined with respect to the longitudinal axis of the outer cover 80 and inclined with respect to the inner surface of the side wall.

The trailing face 114 of the projection 110 in the embodiment shown extends substantially parallel to the longitudinal axis of the outer cover and is oriented in a plane parallel to the radius of the outer cover to extend radially outward. FIG. 7 is an end view of the projections 110 showing the trailing face 114 and the leading face 112 and the orientation relative to the ribs 92.

During use, the hub is threaded onto the threaded end of the delivery pen by rotating the outer cover in the direction of arrow 116 where the leading face 112 of the outer cover engages the leading face 94 of the hub 82. The inclined leading faces 94 and 112 contact each other to rotate the hub and screw the hub onto the delivery pen. Once the hub is tightened onto the delivery pen, the resistance to the outer cover relative to the hub allows the inclined face of the projections 110 to slide over the inclined face of the ribs 92 to prevent over tightening and over torqueing of the hub on the delivery pen. The sliding of the projection 110 over the ribs 92 produces tactile and/or audible sensation to the user to indicate the hub is threaded correctly onto the delivery pen. The outer cover is removed to expose the needle for delivering the medication to the patient. After delivering the medication, the outer cover is returned onto the hub where the projections engage the ribs on the hub. The outer cover rotates in the direction of arrow 118 where the trailing faces 96 and 114 of the projections and the ribs engage to unscrew the hub from the delivery pen. The hub is separated from the delivery pen and discarded.

Figure 10:
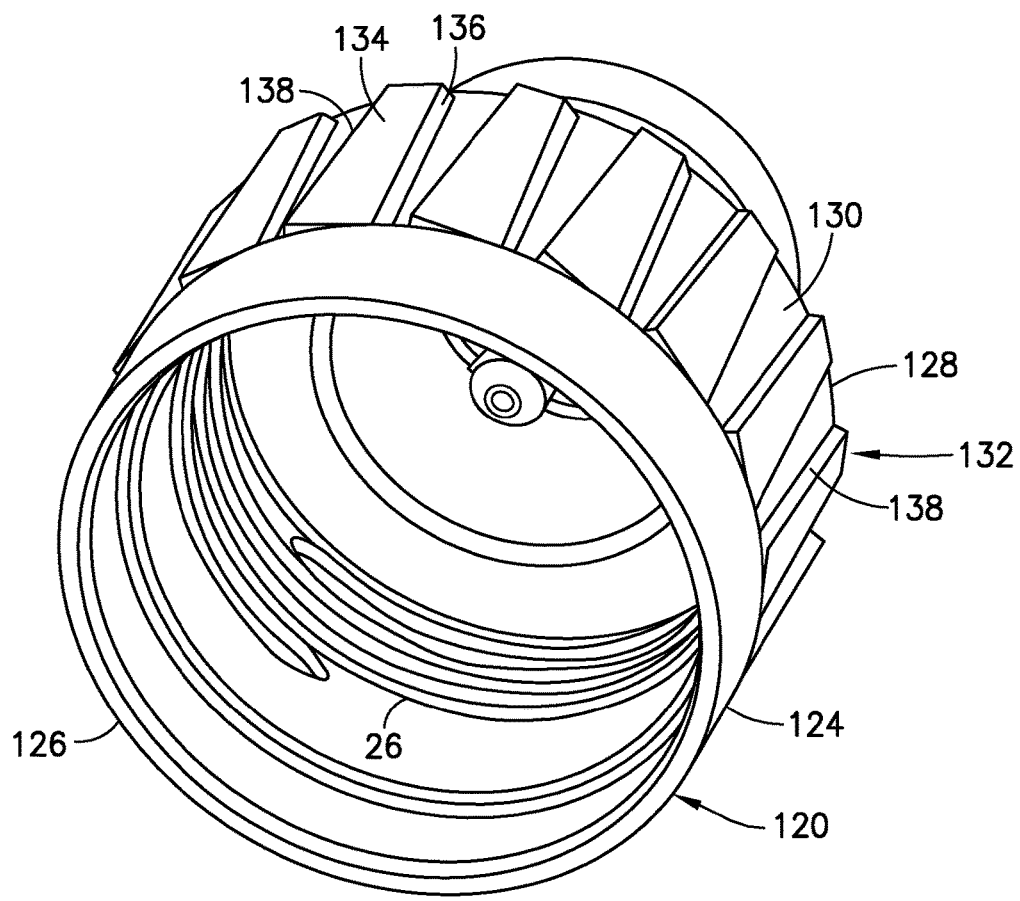
FIG. 10 is an end perspective view of the hub and outer cover in another embodiment.
Figure 11:
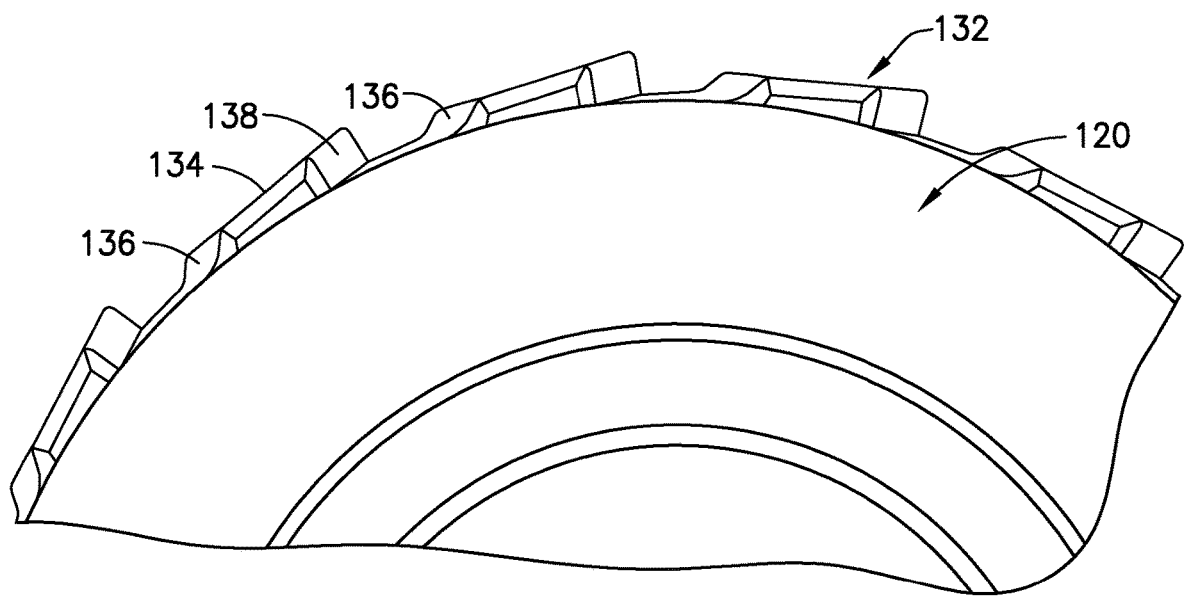
FIG. 11 is an end view showing the ribs on the outside of the hub of FIG. 10.
Figure 12:
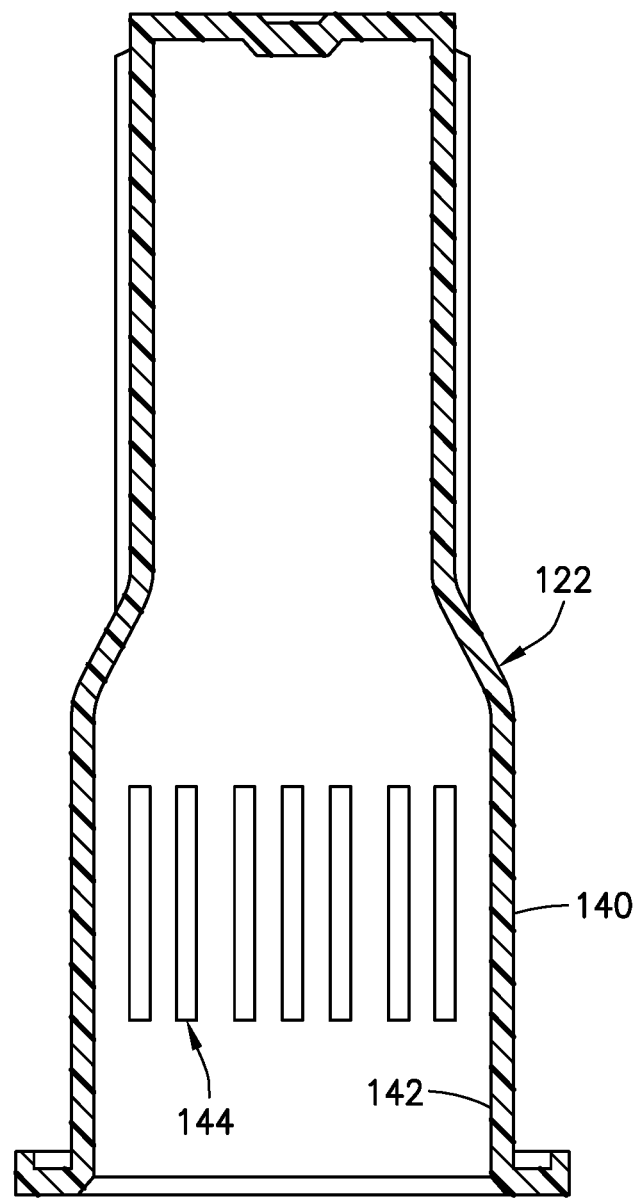
FIG. 12 is a cross sectional view of the hub showing the ribs on the hub and outer cover of the embodiment of FIG. 10.

FIGS. 10-12 show another embodiment of the hub 120 and outer cover 122. The hub 120 as shown in FIG. 10 is similar to the hub of the previous embodiments having a skin contact surface during an injection and a needle extending from the distal end. As in the previous embodiments, the hub 120 has a side wall 124 having an open proximal end 126 and distal end 128. The outer surface 130 of the side wall 124 includes a plurality of spaced apart projections 132 forming ribs that extend from the distal end 128 of the side wall toward the proximal end. The projections 132 project radially outward from the outer surface 130 and extend in a direction substantially parallel to a longitudinal axis of the hub 120.

The projections 132 have an outer radial face 134 extending between a leading face 136 and a trailing face 138. The outer radial face 134 is oriented at an inclined angle relative to the outer surface 130 of the side wall 124 so that the trailing face 138 has a radial dimension greater than a radial dimension of the leading face 134. The leading face 134 is formed at an incline relative to the outer surface 130 of the hub 120 and at an incline relative to the outer face 134. As shown in the figures, the inclined leading face 136 forms a sloped surface the outer surface 130 of the hub 120 between the adjacent projections 132 and the inclined outer face 134 of the projection.

Figure 13:
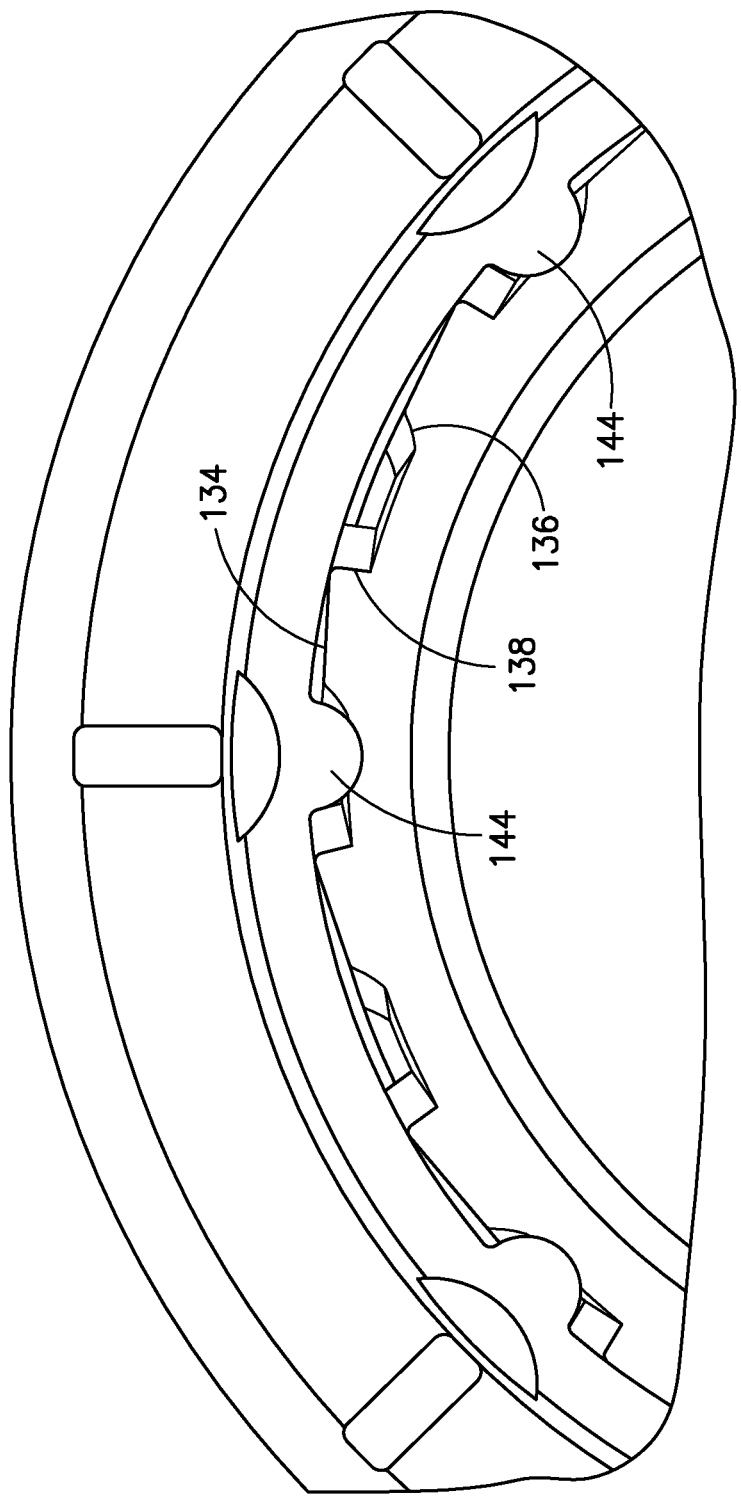
FIG. 13 is a partial end view of one of an embodiment.

The outer cover 122 in the embodiment shown has a side wall 140 complementing the side wall 124 of the hub 120 to fit over the hub 120. The side wall 140 has an inner surface 142 with a plurality of ribs 144 that mate with the projections 132. In the embodiment shown, the ribs 144 extend in a longitudinal direction substantially parallel to the longitudinal axis of the hub 120. In other embodiments, the ribs 144 can be oriented at an angle relative to the longitudinal axis of the outer cover. The ribs 144 as shown in FIG. 13 have a rounded, convex outer surface forming a substantially semicircular shape.

The hub 120 is attached to the threaded end of the delivery device as in the previous embodiment by rotating the outer cover 122 in the direction of arrow 146 to thread the hub 120 onto the delivery device. The ribs 144 engage the leading face 136 of the projections 132 to thread the hub onto the delivery pen. After the hub is tightened onto the delivery pen the ribs 144 slide over the inclined leading face 136 to limit torque applied to the hub and prevent over tightening. The sliding movement of the ribs 144 over the leading face 136 produce a tactile and/or audible sensation to indicate the hub is seated on the delivery pen and is ready for use. The outer cover 122 is removed to expose the needle for injecting the medication into the patient. After use, the outer cover is placed on the hub to unscrew the hub form the delivery pen. By rotating the outer cover 122 in the direction of arrow 148 the ribs 144 engage the trailing face 138 of the respective projection 132 to separate the hub from the delivery pen.

Figure 14:
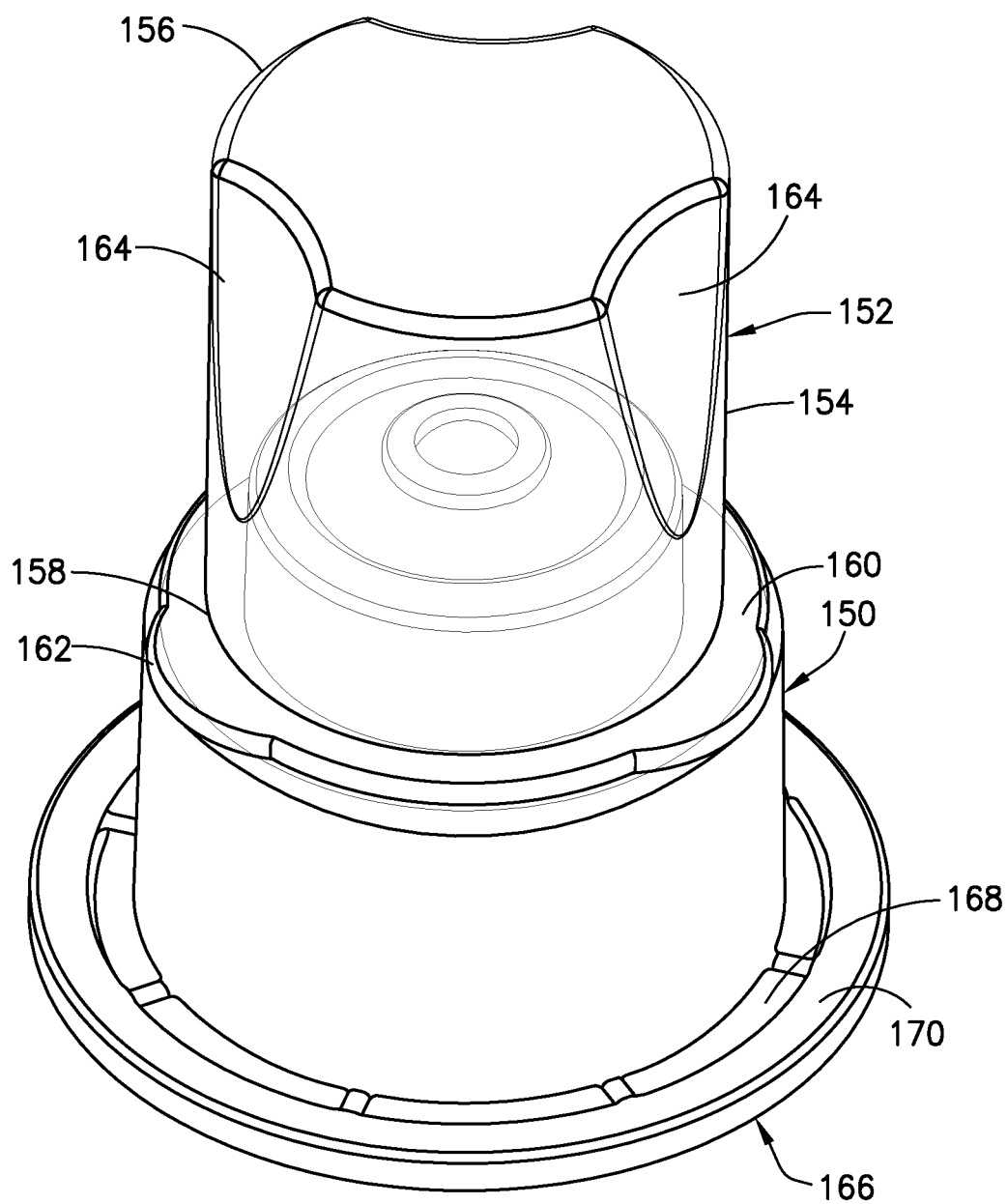
FIG. 14 is a perspective view showing the needle shield on the pen needle in a further embodiment.

FIGS. 14-19 show various forms of the outer cover of the pen needle having configurations to assist the user in gripping the outer cover. In the embodiment of FIG. 14, the pen needle includes a hub 150 having a substantially similar configuration to the previous embodiments and an outer cover 152. The hub supports a needle as shown in the previous figures. The outer cover 152 has a side wall 154 with a distal end 156 and an open proximal end 158. The open proximal end 158 has dimension to fit over the needle bearing post of the hub as shown in FIG. 14 by a friction fit or interference fit. As shown in FIG. 14, a radial flange 160 extends outwardly from the proximal end 158 to assist the user in manipulating the outer cover. As shown in FIG. 14, the radial flange 160 has outwardly extending projecting portions 162 that extend outwardly a distance greater than the radial dimension of the post to assist the user in removing the outer cover 152 from the hub after the hub is threaded onto the delivery pen.

The side wall 154 has recessed portions 164 extending from the distal end 156 toward the proximal end. The recessed portions 164 have concave curved configuration that to form a teardrop shaped recess to assist the user in gripping the outer cover for removing the outer cover from the hub and placing the outer cover back onto the hub after use.

As shown in FIG. 14, the hub 150 has a closure 166 that mates with open proximal end of the hub to cover the proximal end of the needle until ready for use. The closure 166 has a cylindrical side wall that complements the inner surface of the hub and mates with the hub by a friction fit or interference fit. An outwardly extending flange 168 mates with the end of the side wall of the hub to position the closure 166 on the hub. As shown, the flange 168 has an enlarge lip 170 extending in the distal direction to assist the user in handling the closure 166.

Figure 15:
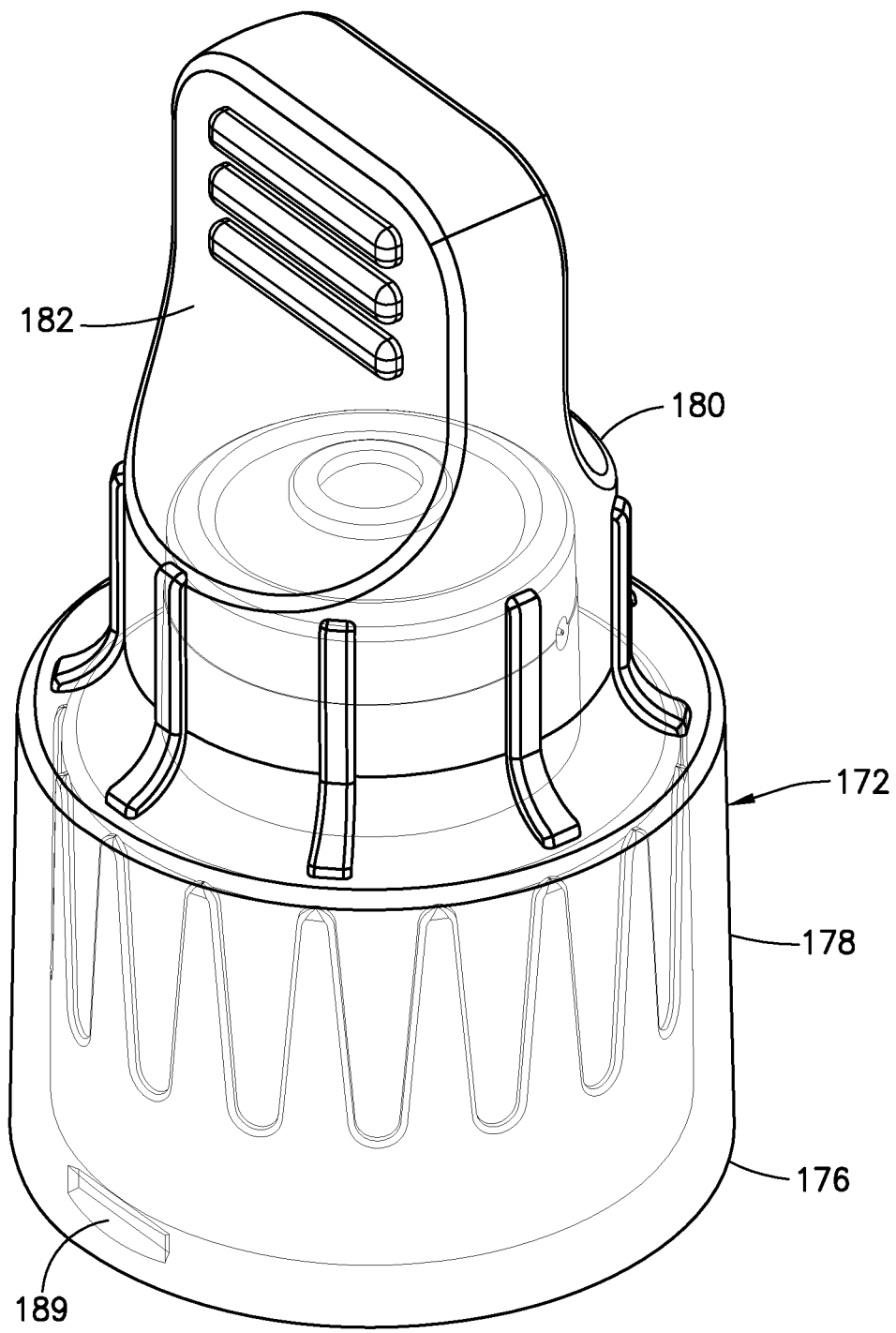
FIG. 15 is a perspective view showing the needle shield on the pen needle in still another embodiment.
Figure 16:
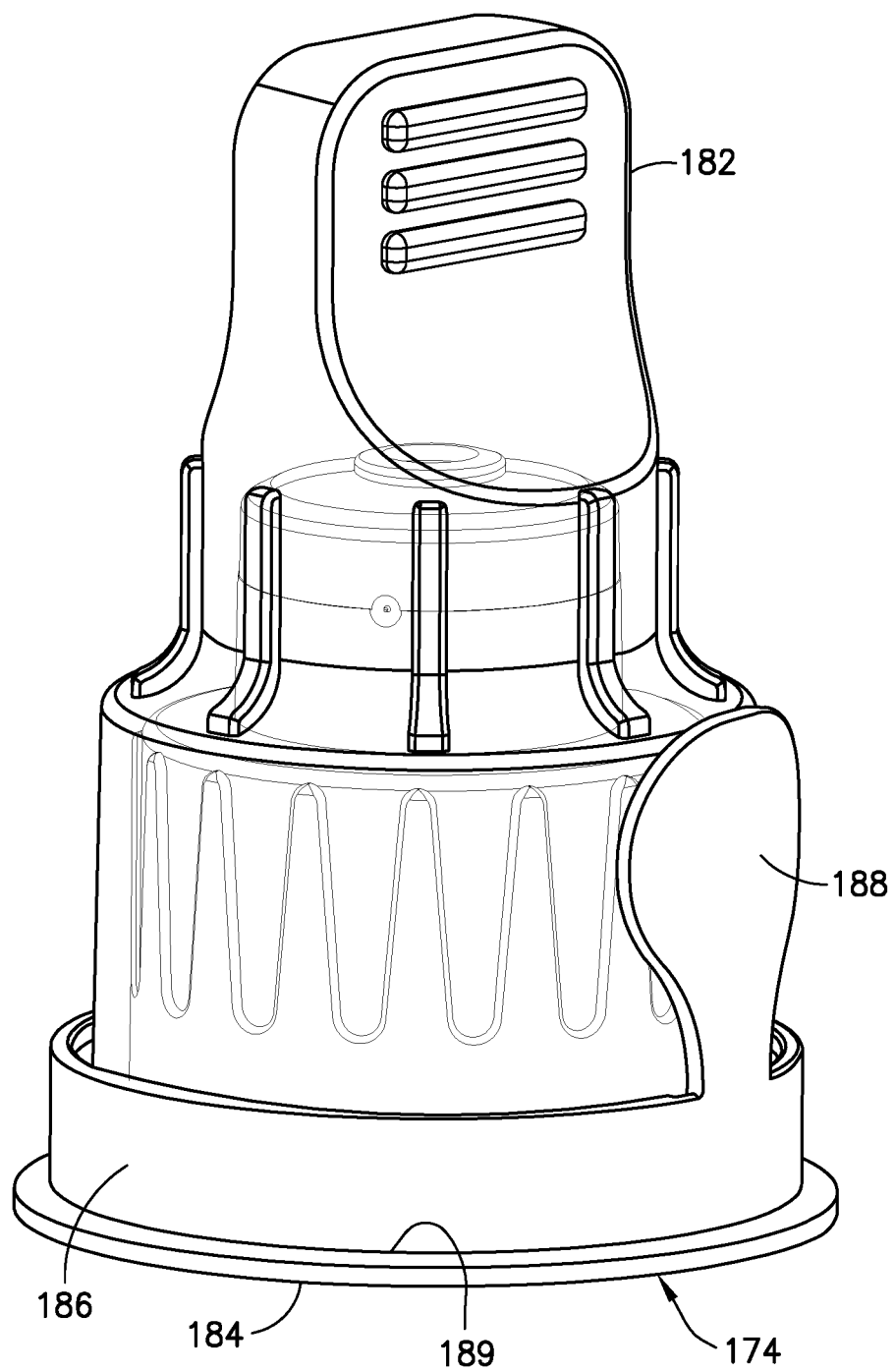
FIG. 16 is a perspective view showing the needle shield on the pen needle in a further embodiment.

FIGS. 15 and 16 illustrate another embodiment of the pen needle where an outer cover 172 encloses the hub and a removable closure 174 connects to the outer cover 172 to enclose the hub. The hub supports a needle, which is not illustrated for clarity. The closure 174 can be used in combination with the pen needle shown in FIGS. 1-5 and the pen needle shown in FIGS. 6-9 and the pen needle of FIGS. 10-13. The outer cover 172 has a proximal end 176 with a substantially cylindrical side wall portion 178 and distal end 180. The distal end 180 is formed with converging surfaces forming outer flat portions 182 for gripping the outer cover. A detent 189 can be included on the inner surface of the wall 178 and extending inwardly to retain the needle hub in the outer cover when the closure is separated as shown in FIG. 15. The outer cover 172 can include the projections 110 for interacting with the outer surface of the needle hub as in the pen needle of FIGS. 6-9.

The closure 174 in the embodiment shown has an end wall 184 with an annular side wall 186 that mates with the open proximal end of the outer cover 172. The side wall 186 has an inner dimension to fit onto the outer surface of the side wall portion 178 by a friction fit. A tab 188 extends from the annular side wall 186 for gripping the closure to assist in removal. The tab 188 in the embodiment shown has a curvature corresponding to the curvature of the annular side wall 186. The side wall 186 is connected to the end wall 184 by a frangible or breakable line 189. The tab 188 is pulled by the user to separate the side wall 186 along the breakable line 189 from the end wall 184 where the end wall 184 can be separated from the outer cover 182.

Figure 17:
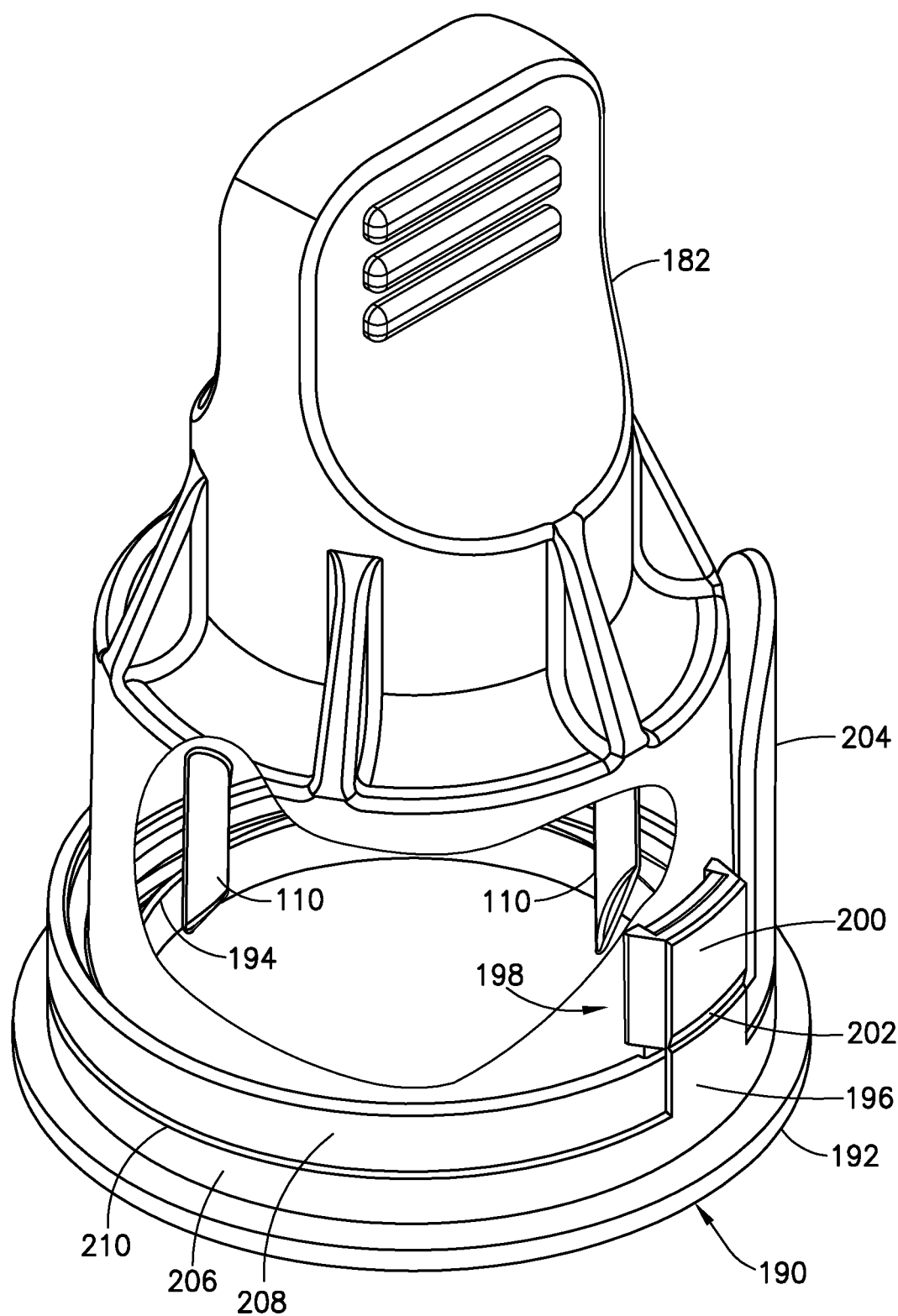
FIG. 17 is a perspective view showing the end cap of FIG. 16 positioned on the open end of the outer cover.
Figure 18:
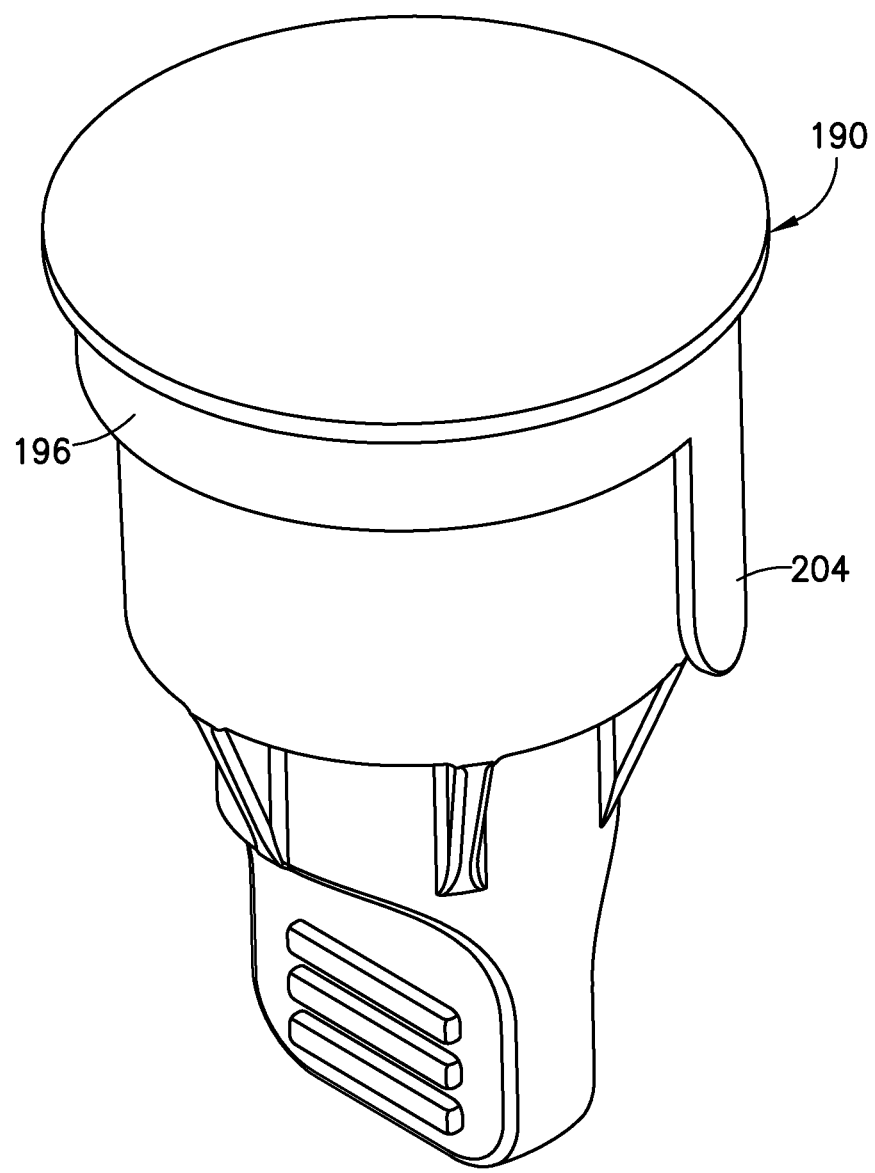
FIG. 18 is a perspective view showing the needle shield on the pen needle in another embodiment.
Figure 19:
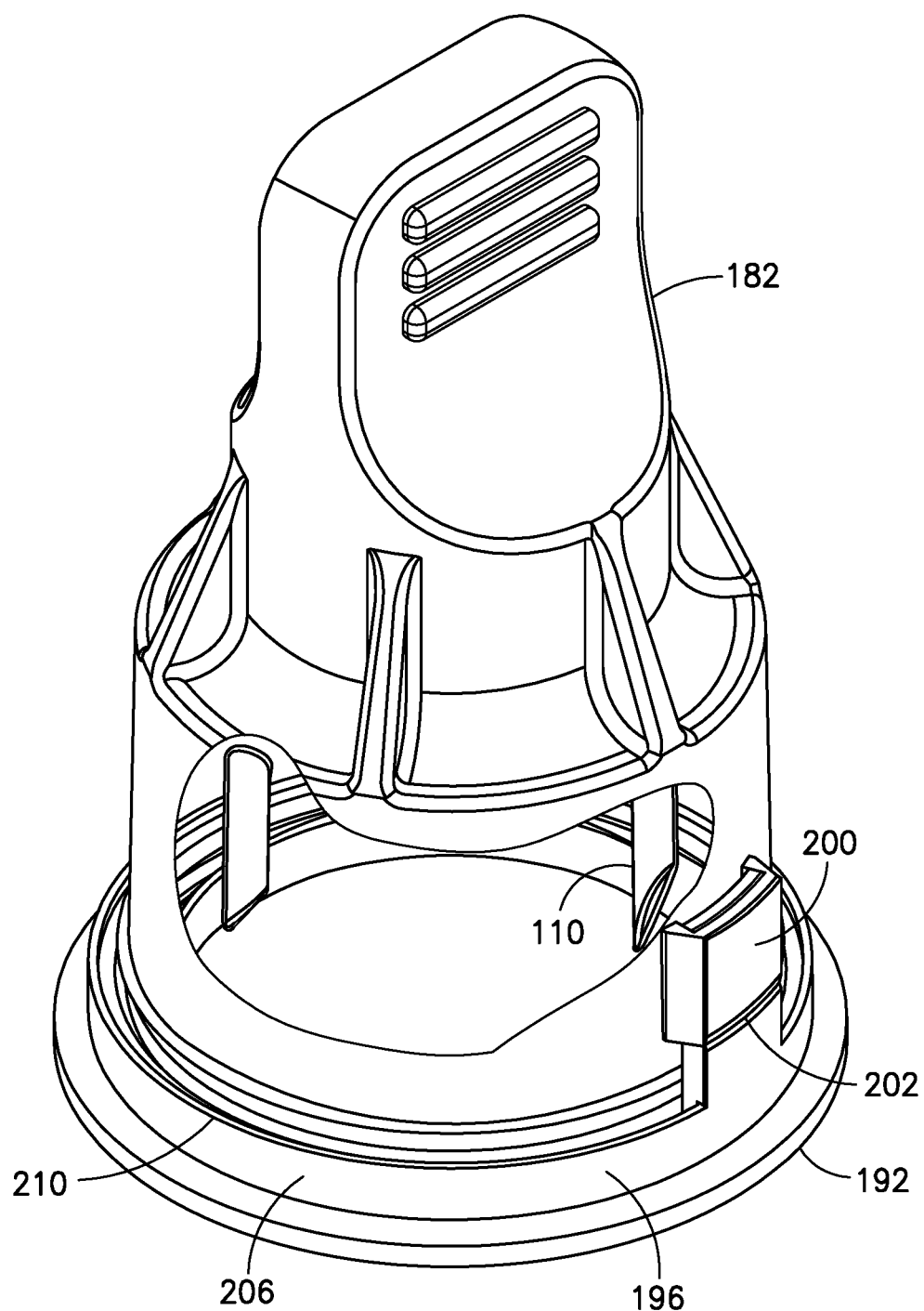
FIG. 19 is a perspective view showing the pen needle of FIG. 17 after use.

FIGS. 17-19 show another closure for the outer cover. The outer cover in the embodiment of FIGS. 17-19 is substantially the same as in the embodiment of FIG. 16. The closure 190 can be used with the pen needle of FIGS. 1-5, the pen needle of FIGS. 6-9 and the pen needle of FIGS. 10-13. The closure 190 has an end wall 192 with an inner annular wall 194 and an outer annular wall 194 forming an annular space for receiving the proximal end of the outer cover and attaching the closure to the outer cover 196. The annular wall 194 includes a bottom portion 206 attached to the end wall 192 and a removable portion 208 connected to the end wall 194 by a frangible break line 210. The outer cover 196 includes a tamper evident member 198 to indicate use of the pen needle. The tamper evident member 198 includes a finger tab 204 attached to a removable portion 208 of the side wall 194. Pulling on the finger tab 204 separates the removable portion 208 from the bottom portion 206 so that the end wall 192 can be separated from the outer cover 182 and provide an indication that the pen needle has been used or opened. A tab 200 is connected to the outer annular wall 194 by a flexible hinge line 202. The tab 200 is attached to the side wall of the outer cover 196 by an adhesive, welding or other attachment means. In one embodiment, the tab 200 is permanently fixed to the side wall of the outer cover 196. During use, the end wall 192 hinges to an open position to allow access to the pen needle. After use, the used pen needle can be returned to the outer cover and the end wall 192 pivoted to the closed position to enclose the used pen needle as shown in FIG. 19. The bottom side of the end wall 192 can include engraved indicia as desired such as indicia identifying the dimensions of the needle.

Figure 20:
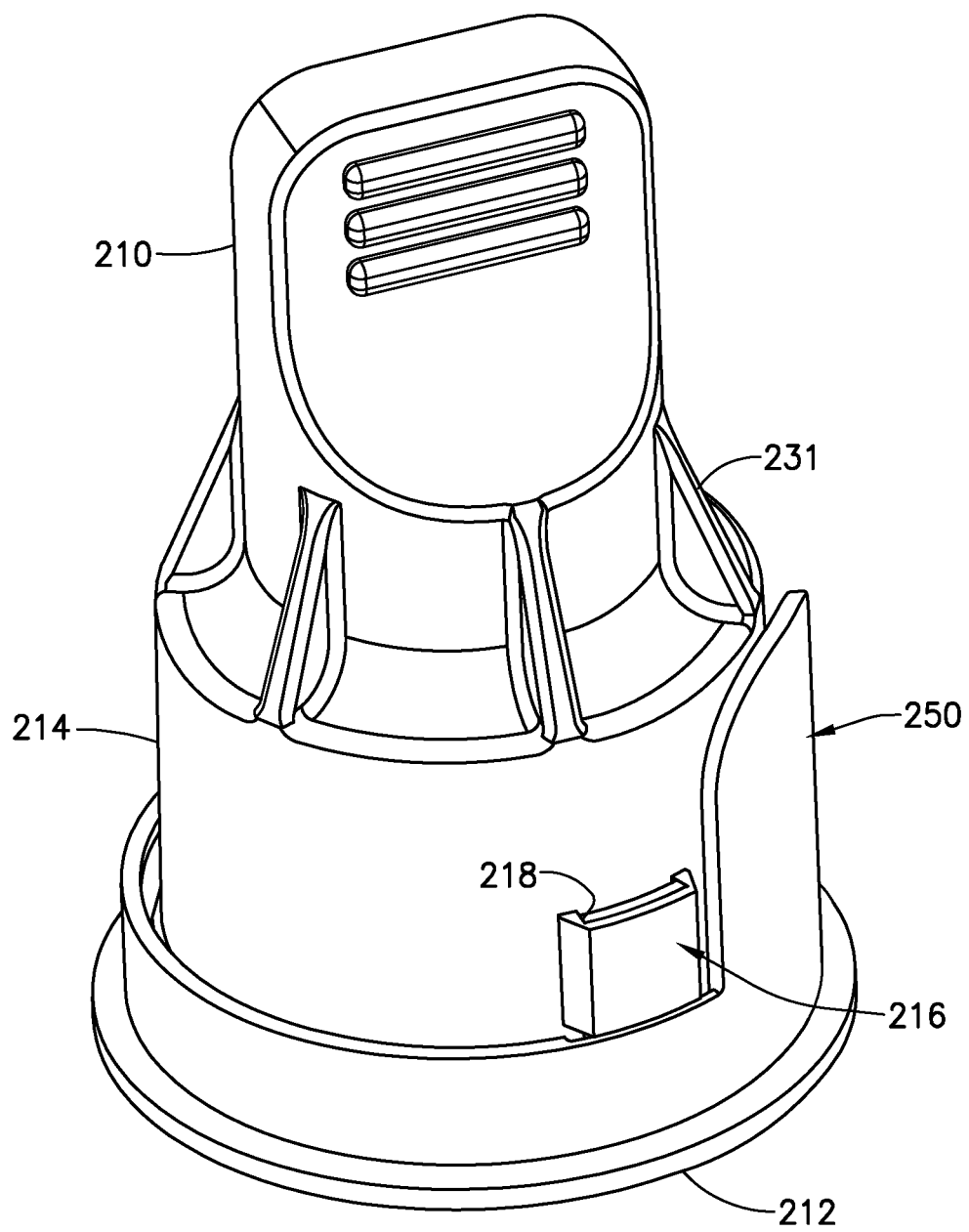
FIG. 20 is a perspective view of the pen needle in a another embodiment.
Figure 22:
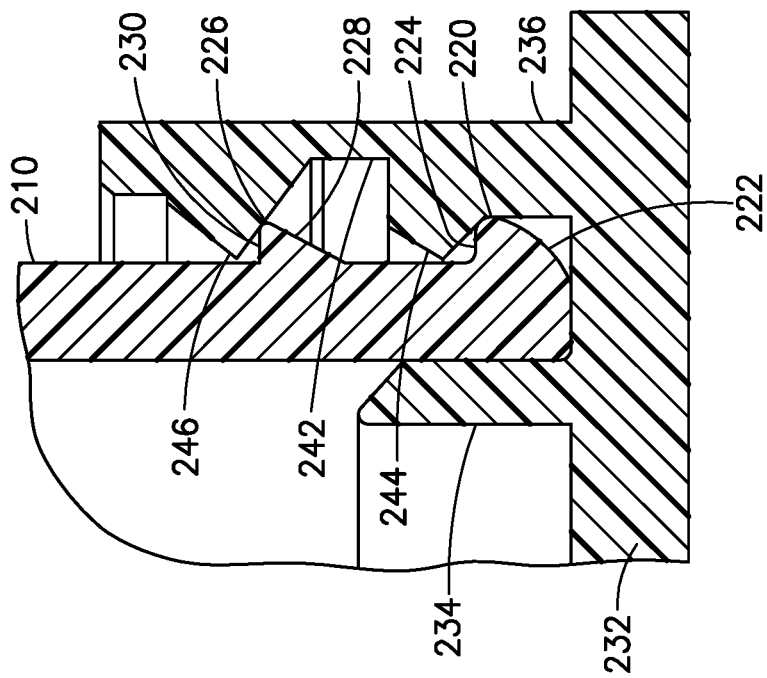
FIG. 22 is an enlarged view of the connection between the outer cover and the base of the pen needle of FIG. 20.
Figure 21:
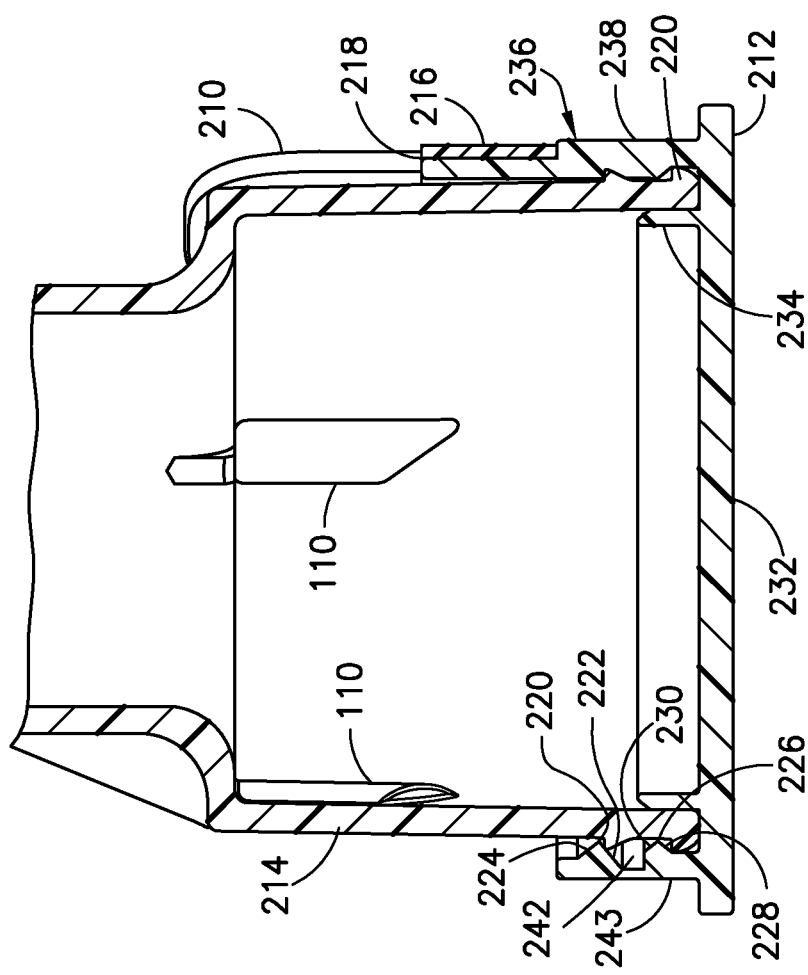
FIG. 21 is a partial cross sectional view of the pen needle of FIG. 20.

FIGS. 20-25 show another embodiment of the pen needle including an outer cover 210 and a closure 212. The outer cover can be used with the pen needle of FIGS. 1-6 or the pen needle of FIGS. 6-9 or the pen needle of FIGS. 10-13. The outer cover 210 has a shape similar to the previous embodiment. In the embodiment shown, the outer cover 210 has a side wall 214 and an open proximal end that couples with the closure 212. As shown in FIG. 20 and FIG. 21, the side wall 214 has a band 216 integrally formed with the side wall 214 and forming an open slot 218 on the side wall. As shown in FIG. 21, the outer surface of the side wall 214 at the proximal open end includes an outwardly extending flange 220 having an inclined bottom surface 222 and a flat top surface 224. An intermediate flange 226 is spaced axially from the flange 220 in the distal direction and has a similar configuration with an inclined bottom face 228 and a flat top face 230. Axially oriented ribs 231 on the outer surface of the cover 210 to assist the user in manipulating the outer cover.

The closure 212 has a bottom wall 232 with an inner annular flange 234 having an outer dimension complementing the inner dimension of the wide wall 214 of the outer cover 210 as shown in FIG. 21. An outer annular flange 236 is spaced radially outward from the inner flange 234 a distance corresponding substantially to the thickness of the side wall 214 and flanges 229 and 226 as shown in FIG. 21. The outer annular flange 236 has an outer surface 238 and an inner surface 240. The inner surface 240 has an annular recess 242 defined by a proximal inwardly extending flange 244 and a distal inwardly extending flange 246 spaced from the flange 242. The recess 242 forms a thin breakable line in the outer annular flange 236. The proximal flange 244 has proximal face for mating with the flange 220 and the distal flange 246 has a proximal face for mating with the intermediate flange 226 as shown in FIG. 21.

Referring to FIG. 20 and FIG. 21 the outer annular wall 234 has a tab 248 received in the slot 218 to tether the closure 212 to the outer cover 210. The tab 248 is sufficiently flexible to allow the tab to bend so that the closure can pivot to an open position. The tab 248 can be coupled to the outer cover by a friction fit or interference fit in the slot 218 or by an adhesive. In one embodiment, the tab 248 can be retained by a friction fit and can be removed and separated from the slot if desired.

Figure 23:
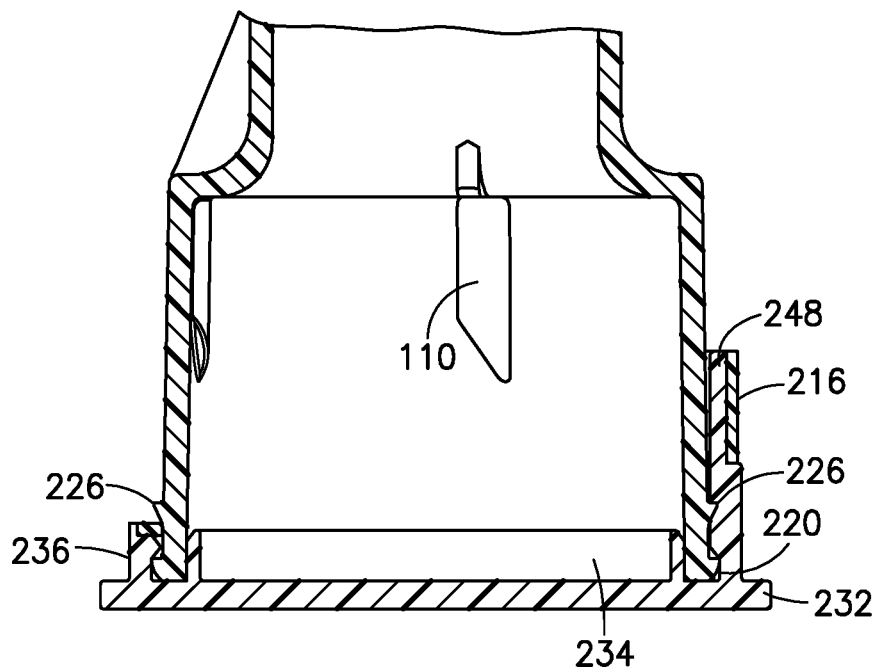
FIG. 23 is partial cross sectional view showing the peel tab removed in the embodiment of FIG. 20.
Figure 24:
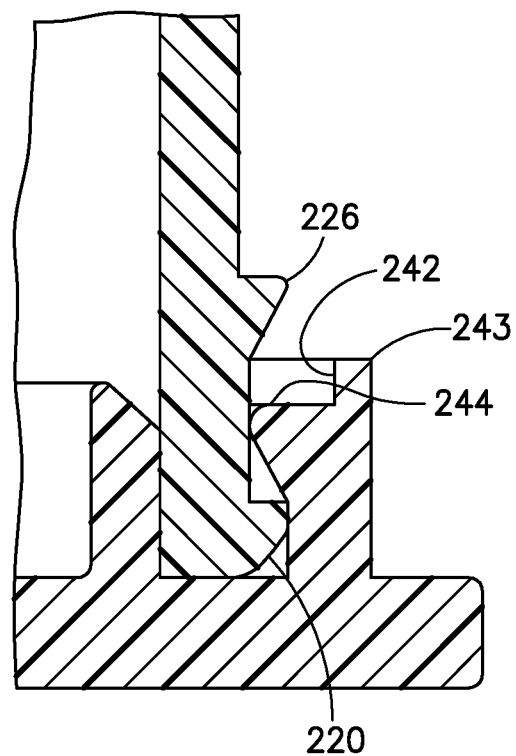
FIG. 24 is an enlarged cross sectional view of the connection between the outer cover and the base of FIG. 23.
Figure 25:
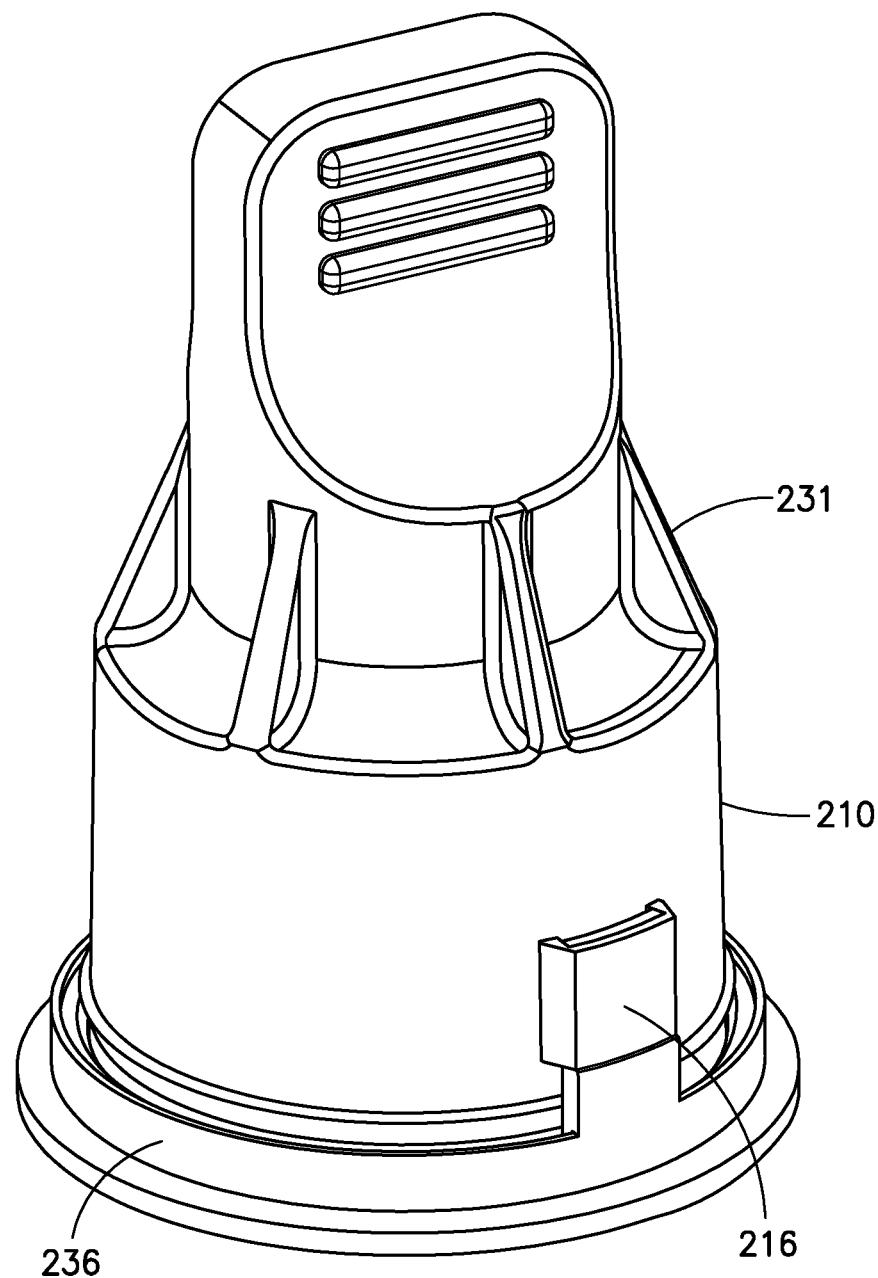
FIG. 25 is perspective view of the outer cover and base of the embodiment of FIG. 20.

A pull-tab 250 is coupled to the distal end of the outer wall 236. In the embodiment shown, the pull-tab 250 is integrally formed with the outerwall 236. The inwardly extending flanges 244 and 246 on the outer wall engage the flanges 222 and 224 of the outer cover to couple the closure to the outer cover. The pull-tab 250 can be pulled by the user to separate a distal portion of the outer wall defined by a break line 243 along the recess 242 as shown in FIGS. 23-25. The tab 248 remains attached to the outer wall 236 and is received in the slot 218 as shown in FIG. 25. The closure 212 can be separated from the cover 210 to open the cover while being tethered to the cover so that a pen needle can be removed for use in an injection of a medication. After use, the pen needle is returned to the outer cover and the closure closed to position shown in FIG. 25. The removal of the pull-tab 250 provides a tamper indicator to show the user that the pen needle has been previously opened. The closure can be separated from the cover to open the cover so that the pen needle can be removed for use in an injection of a medication. After use, the pen needle is returned to the outer cover and the closure closed to the position shown in FIG. 26.

Figure 26:
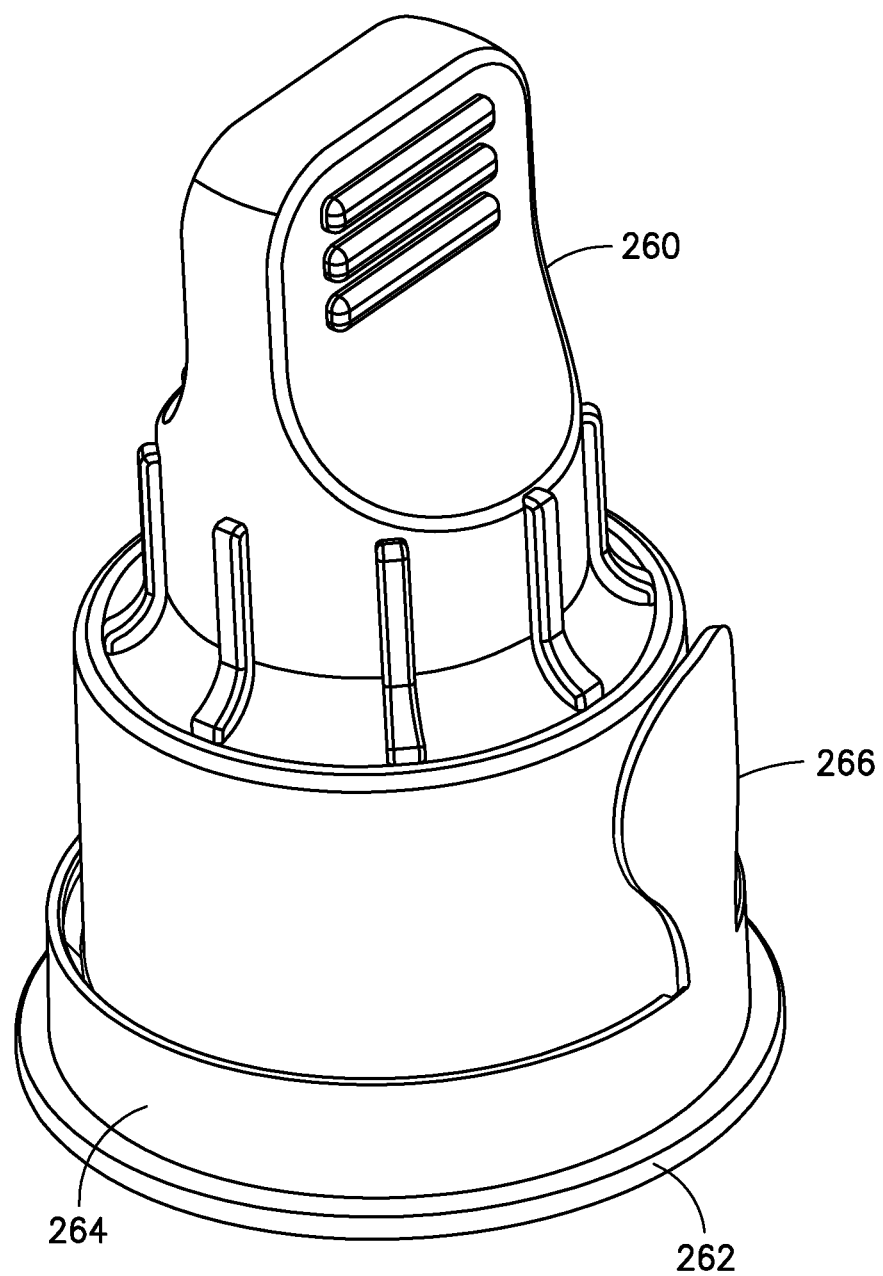
FIG. 26 is a perspective view of the pen needle in a further embodiment.
Figure 27:
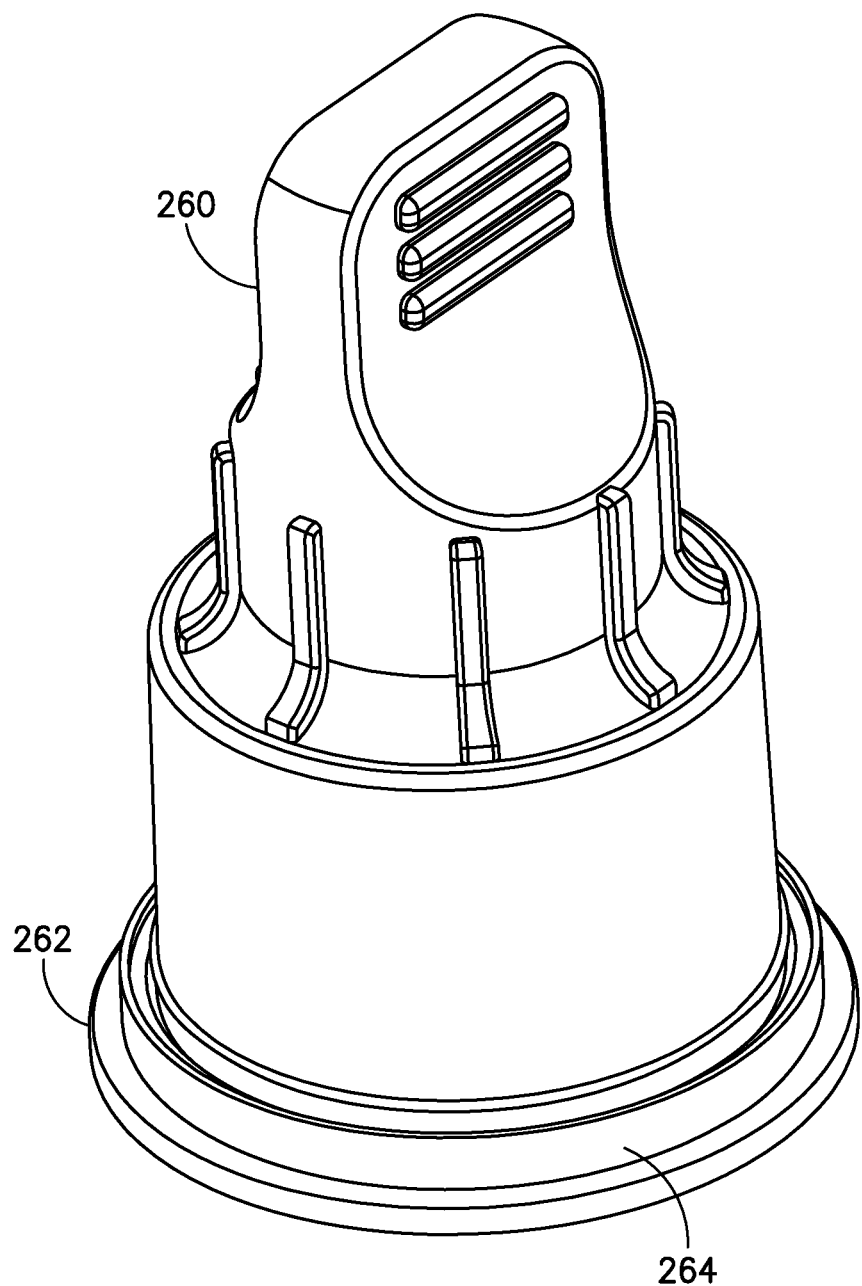
FIG. 27 is a perspective view of the pen needle of FIG. 26 with the peel tab removed.

FIGS. 26 and 27 show another embodiment of the cover 260 and closure 262 that are similar to the embodiment of FIGS. 20-25 with the exception of the tab to tether to the closure to the outer cover and can be used with the pen needles described herein. The closure 262 has an outer wall 264 with inwardly extending annular flanges that mate with corresponding annular flanges in a manner similar to the previous embodiment shown in FIG. 23. A pull-tab 266 is included in a manner similar to the previous embodiment. An annular recess formed between the flanges on the outer wall define a frangible break line. Pulling on the pull-tab 266 by the user separates the breakable section of the outer wall 264 as shown in FIG. 27 where the closure 262 can be separated from the outer cover 262. In the embodiment shown in FIGS. 26 and 27, the break line completely circles the outer wall of the closure so that the top portion of the outer wall can be removed as shown in FIG. 27.

In the embodiments, the components of the hub and shield are typically injection molded plastic, such as acrylonitrile butadiene styrene (ABS), polyethylene, polypropylene, or the like. The needle can be a surgical grade stainless steel. Other materials and methods of manufacture known to those of ordinary skill in the art of medication pen technology may be adapted for use herein without departing from the scope of the invention. To assemble the parts, the hub assembly may be constructed with the needle separately, with adhesive applied in the interface area to secure the cannula to the hub, and this sub-assembly may then be assembled with the other components.

The foregoing description of the preferred embodiments is not to be deemed limiting of the invention, which is defined by the following claims. The foregoing description should provide the artisan of ordinary skill with sufficient information to practice variants of the embodiments described. The features of the different embodiments can be used in conjunction with the features of other embodiments. By way of example the embodiments of the outer cover can be used with the various embodiments of the connections between the outer cover and the hub. Features and improvements described in dependent claims or in connection with one embodiment may be combined with those of another independent claim or another embodiment, provided they are not inconsistent therewith, without departing from the scope of the invention.

The invention claimed is:

1. A pen needle, comprising:
   a hub having an outer surface having a plurality of ribs extending longitudinally with respect to said hub and projecting radially outward, a distal end, a side wall with an inner surface including threads, and an open proximal end, wherein the threads are configured for attachment to a delivery device, wherein said ribs of said hub comprise:
      a leading face at an incline with respect to a longitudinal axis of said hub and at an incline with respect to a radius of said hub;
      a trailing face oriented in a plane substantially parallel to the radius of said hub and parallel to the longitudinal axis of said hub; and
      an outer radial face oriented in an inclined plane relative to an outer radial surface of said hub;
   a needle coupled to said hub and having a distal end extending from said distal end of said hub and a proximal end extending toward the open proximal end of the hub;
   a removable inner shield coupled to said hub, said inner shield having a side wall with an inner surface complementing an outer surface of said hub and where said inner shield is configured for coupling to a distal end of said outer surface of said hub for covering said distal end of said needle, said inner shield having an outer surface with an outer dimension for coupling with an inner surface of said open proximal end of said hub for covering said proximal end of said needle; and
   an outer cover with a dimension to receive said hub, said outer cover having a side wall with an inner surface having a plurality of ribs projecting radially inward, each of said ribs configured to engage a corresponding rib of the plurality of ribs on said hub for connecting said hub to the delivery device by rotation of said outer cover in a first direction and separating said hub from the delivery device by rotation of the outer cover in a second direction, wherein said ribs on said outer cover engage said leading face of said ribs on said hub when rotating said outer cover in the first direction.

2. The pen needle of claim 1, wherein said dimension of said outer surface of said inner shield complements an inner dimension of said open proximal end of said hub.

3. The pen needle of claim 2, wherein said inner shield is coupled to an inner surface of said open proximal end of said hub by a friction fit.

4. The pen needle of claim 3, wherein said side wall of said inner shield includes at least one rib projecting radially outward from the side wall, wherein said at least one rib engages said inner surface of said hub to retain said inner shield in said open proximal end of said hub.

5. The pen needle of claim 1, wherein said trailing face of said ribs of said hub has a radial dimension greater than a radial dimension of said leading face of said ribs of said hub.

6. The pen needle of claim 5, wherein said ribs of said outer cover have a rounded convex shape.

7. The pen needle of claim 1, further comprising a closure cap coupled to an open end of said outer cover, and where said closure cap has a tamper evident member.

8. The pen needle of claim 7, wherein said closure cap includes an end wall, and an annular side wall having an inner dimension for coupling with said open end of said outer cover, and a tab extending from said annular side wall.

9. The pen needle of claim 8, wherein said annular side wall of said closure cap has a frangible portion to separate said annular side wall from said end wall.

10. The pen needle of claim 8, wherein said annular side wall has a bottom portion attached to said end wall, and a removable portion formed by a frangible portion between said bottom portion and said removable portion.

11. The pen needle of claim 10, wherein said bottom portion is coupled to said outer cover by a hinge.

12. The pen needle of claim 10, wherein said bottom portion of said annular side wall has an inwardly extending flange for engaging an outwardly extending flange on said outer cover.

13. The pen needle of claim 1, wherein said side wall of said hub has a flexible portion that can flex radially outward for separating said hub from a threaded end of the delivery device.

14. The pen needle of claim 13, wherein said side wall has a longitudinally extending slot to define said flexible portion.

15. The pen needle of claim 13, wherein said outer cover has an inwardly extending projection to engage said open proximal end of said hub to assist separation of said hub from the delivery device.

* * * * *